(12) United States Patent
Shelke et al.

(10) Patent No.: US 11,564,888 B2
(45) Date of Patent: *Jan. 31, 2023

(54) EXTENDED RELEASE COMPOSITIONS COMPRISING TRIHEXYPHENIDYL

(71) Applicant: KASHIV SPECIALTY PHARMACEUTICALS, LLC, Bridgewater, NJ (US)

(72) Inventors: Namdev B. Shelke, Hillsborough, NJ (US); Siva Ram Kiran Vaka, Piscataway, NJ (US); Navnit H. Shah, Monmouth Junction, NJ (US); Dipen Desai, Whippany, NJ (US); Wantanee Phuapradit, Montville, NJ (US)

(73) Assignee: Amneal Complex Products Research LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/272,481

(22) PCT Filed: Sep. 19, 2019

(86) PCT No.: PCT/US2019/051928
§ 371 (c)(1),
(2) Date: Mar. 1, 2021

(87) PCT Pub. No.: WO2020/061308
PCT Pub. Date: Mar. 26, 2020

(65) Prior Publication Data
US 2021/0330657 A1  Oct. 28, 2021

Related U.S. Application Data

(60) Provisional application No. 62/734,804, filed on Sep. 21, 2018, provisional application No. 62/848,996, filed on May 16, 2019.

(51) Int. Cl.
| | | |
|---|---|---|
| *A61K 9/50* | (2006.01) | |
| *A61K 9/28* | (2006.01) | |
| *A61K 9/20* | (2006.01) | |
| *A61K 31/4453* | (2006.01) | |
| *A61K 9/00* | (2006.01) | |
| *A61K 47/12* | (2006.01) | |

(52) U.S. Cl.
CPC ......... *A61K 9/2886* (2013.01); *A61K 9/0053* (2013.01); *A61K 9/2054* (2013.01); *A61K 9/501* (2013.01); *A61K 9/5047* (2013.01); *A61K 9/5078* (2013.01); *A61K 9/5089* (2013.01); *A61K 31/4453* (2013.01); *A61K 47/12* (2013.01)

(58) Field of Classification Search
None
See application file for complete search history.

(56) References Cited

U.S. PATENT DOCUMENTS

| | | | | |
|---|---|---|---|---|
| 5,326,570 A | * | 7/1994 | Rudnic | A61K 9/5084 424/490 |
| 2007/0225366 A1 | * | 9/2007 | Xiang | A61P 25/00 514/534 |
| 2008/0069878 A1 | * | 3/2008 | Venkatesh | A61K 9/5026 514/355 |
| 2009/0196935 A1 | | 8/2009 | Ahmed et al. | |
| 2011/0287096 A1 | * | 11/2011 | Gorukanti | A61K 31/506 514/252.19 |
| 2011/0311626 A1 | * | 12/2011 | Venkatesh | A61P 1/08 424/494 |
| 2015/0037405 A1 | * | 2/2015 | Kulkarni | A61K 9/4833 424/458 |

FOREIGN PATENT DOCUMENTS

| | | |
|---|---|---|
| WO | WO 2010096820 | 8/2010 |
| WO | WO 2016087952 | 6/2016 |

OTHER PUBLICATIONS

Pharmacokinetic Evaluation of a Sustained-Release Formulation of Trihexyphenidyl in Healthy Volunteers. Journal of Pharmaceutical Sciences, vol. 77, Nov. 9, September (Year: 1988).*
K Vilnay Kumar et al., Formulation and Evaluation of Extended Release Trihexyphenidyl Hydrochloride hard gelatin capsules. International Journal of Pharmaceutical Sciences and Nanotechnology; vol. 4, Issue 1, Apr.-Jun. 2011.
Cheung et al., Pharmacokinetic Evaluation of a Sustained-Release Formulation of Trihexyphenidyl in Healthy Volunteers; Medical research Division and Lederle Laboratories, American Cynamid Company, Apr. 26, 1988.
International Search Report and Written Opinion dated Jan. 13, 2020 in PCT/US2019/051928.

* cited by examiner

*Primary Examiner* — Susan T Tran
(74) *Attorney, Agent, or Firm* — Amneal Complex Products Research LLC; Vandana Awasthi

(57) ABSTRACT

The present disclosure provides extended release trihexyphenidyl compositions suitable for once- or twice-daily administration. The compositions comprise a core comprising organic acid that is coated with at least one drug layer comprising trihexyphenidyl hydrochloride, and a functional coat over the drug-layered core. The extended release compositions of the disclosure provide extended release of trihexyphenidyl hydrochloride, with reduced $C_{max}$, and a $C_{min}:C_{max}$ ratio of ≥0.4, while maintaining a therapeutically effective concentration for a period of at least about 16 hours. The compositions of the disclosure improve solubility of trihexyphenidyl hydrochloride, at a pH of greater than or equal to 5, to maintain its minimum effective concentration at such pH. In certain embodiments, the compositions of the disclosure comprise an IR drug layer to provide extended release with a minimal lag time, while maintaining a therapeutically effective concentration of trihexyphenidyl hydrochloride for a period of at least about 16 hours.

17 Claims, 9 Drawing Sheets

EXTENDED RELEASE COMPOSITIONS COMPRISING TRIHEXYPHENIDYL

1. RELATED APPLICATIONS

Figure 1:
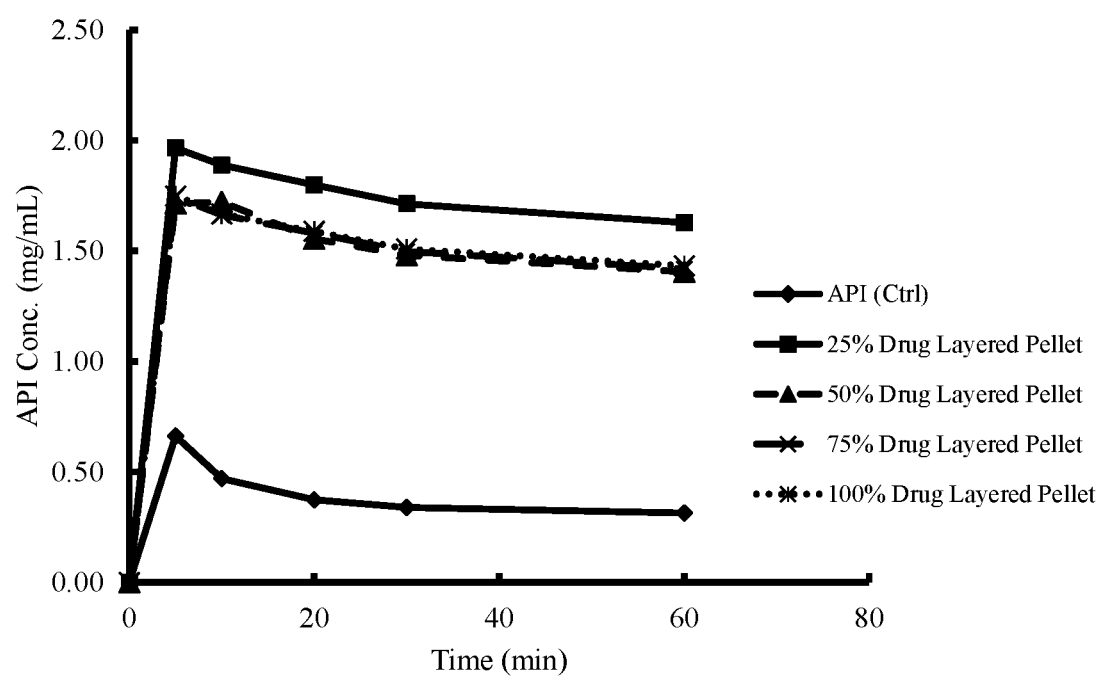

This application is a U.S. National Stage Patent Application under 35 U.S.C. § 371 of International Application No. PCT/US2019/051928 filed on Sep. 19, 2019, which claims priority to U.S. Provisional Patent Application No. 62/734,804, filed Sep. 21, 2018, and U.S. Provisional Patent Application No. 62/848,996, filed May 16, 2019, the disclosures of which are incorporated by reference in their entireties.

2. TECHNICAL FIELD

The present disclosure provides extended release (ER) trihexyphenidyl (THP) compositions suitable for once or twice daily administration. The compositions provide an acid microenvironment that improves the solubility of trihexyphenidyl (THP) at a pH greater than or equal to about 5, and helps to maintain therapeutic concentrations of THP over extended periods of time. In certain embodiments, the disclosure provides ER THP compositions containing an immediate release (IR) drug layer containing THP. Such compositions (1) minimize lag time and provide extended release of THP within the therapeutic range, and (2) maintain a stable therapeutic plasma concentration of the drug for extended periods of time. The compositions of the disclosure reduce drug toxicity and drug-related side effects, compared to marketed THP tablets, by providing trough-to-peak concentration ratios [$C_{min}$ (minimum plasma concentration):$C_{max}$ (maximum plasma concentration) ratio] of greater than or equal to about 0.4. The compositions of the disclosure maintain plasma concentrations of at least about 30%, e.g., about 50% of the $C_{max}$ value for an average time period of about 24 hours post-administration of the ER formulation. The ER trihexyphenidyl compositions of the disclosure include pellets suitable for dosing in capsules, sachets, and as sprinkles on food.

3. BACKGROUND

Trihexyphenidyl, a phenyl propylamine (also known as benzhexol and trihex) is an anticholinergic agent. THP is a synthetic antispasmodic drug that is widely used in the treatment of patients with all forms of parkinsonism, including primary or idiopathic Parkinson's disease, secondary symptomatic parkinsonism (postencephalitic, arteriosclerotic, infection-induced, tumor-induced, trauma-induced, and drug-induced), and involuntary movements due to side effects of certain psychiatric drugs. See, Cheung et al. (1988) "Pharmacokinetic evaluation of a sustained release formulation of trihexyphenidyl in healthy volunteers" *J. Pharm. Sci.,* 77(9):748-50. It is often useful as adjuvant therapy when treating these forms of parkinsonism with levodopa. Additionally, it is indicated for the control of extrapyramidal disorders caused by central nervous system drugs such as dibenzoxazepines, phenothiazines, thioxanthenes, and butyrophenones. Trihexyphenidyl is also used for treating primary dystonia, dystonia associated with cerebral palsy (dyskinetic cerebral palsy), and/or sialorrhea, using extended release THP HCl pellets.

THP, chemically known as α-cyclohexyl-α-phenyl-1-piperidinepropanol, has the following chemical structure.

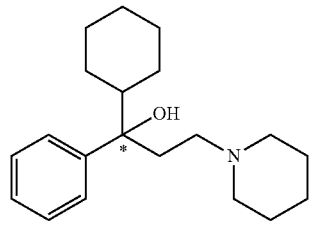 [SMILES: OC(CCN1CCCCC1)(c1ccccc1)C1CCCCC1]

Trihexyphenidyl hydrochloride was introduced as a synthetic drug for treatment of Parkinson's disease in 1949. Dosahay and Schwab (1962) "Slow-release Trihexyphenidyl in Parkinson's Disease" *JAMA,* 180(2):159-61. It has proved to be one of the more useful drugs for the treatment of Parkinson's disease and has been available in 2 mg and 5 mg scored tablets for many years. Corbin (1949) "Trihexyphenidyl: Evaluation of New Agent in Treatment of Parkinsonism" *JAMA,* 141(6):377-82.

The U.S. Food and Drug Administration (FDA) had approved extended release THP hydrochloride capsules (Artane), prior to Jan. 1, 1982 (now discontinued), as well as various immediate release generic forms of THP hydrochloride, for the treatment of parkinsonism and drug-induced parkinsonism.

THP hydrochloride, due to its poor solubility at pH greater than or equal to about 5, exhibits highly variable blood plasma levels after oral administration. The approved and currently marketed IR THP hydrochloride products have side effects, e.g., drowsiness, dizziness or blurred vision, dry mouth, stomach upset, vomiting, diarrhea, constipation, and difficulty in urinating, associated with high peak serum concentrations ($C_{max}$) and low trough-to-peak concentration ratios ($C_{min}:C_{max}$). In elderly individuals, if the dosage strength is too high, the side effects are urinary difficulty and/or retention, confusion, agitation, and hallucinations, particularly during the night. Dosahay and Schwab, supra.

Unlike other compounds employed in the treatment of Parkinson's disease, THP shows little tendency towards an increase in tolerance and can be used with consistent benefit for over ten years. Further, THP is an efficient drug that is safe and has a long period of clinical experience. The above-mentioned advantages of THP make it an ideal candidate for extended release formulations that can provide and maintain reasonably stable therapeutically effective plasma concentrations.

However, trihexyphenidyl has a short plasma half-life (about 3.7 hours), short duration of action, and requires (1) frequent dosing, which results in various side effects associated with high $C_{max}$ and low $C_{min}:C_{max}$ ratios; or (2) dosing at higher strengths as ER dosage forms, which results in various side effects associated with an initial drug release in an amount that is higher than the therapeutic range (e.g., a burst release of the drug) and/or exhibits highly variable blood plasma levels after oral administration due to its poor solubility at a pH greater than or equal to about 5. Thus, it is desirable to develop ER THP compositions that can reduce variations in plasma concentrations of the drug, associated with a reduction in solubility at a pH of greater than about 5, over an extended period of time, and reduce side effects associated with presently approved IR compositions.

There is a need to develop once-a-day extended release THP compositions, which can provide at least a 16-hour, preferably a 24-hour, release profile of trihexyphenidyl hydrochloride, with no burst release, and reduce the side effects of currently marketed IR compositions.

There remains a need to develop once-a-day THP compositions that provide improved drug solubility at pH of greater than or equal to about 5, and provide extended release of the drug for periods of about 12 hours to about 24 hours, e.g., about 16 hours.

There remains a need for ER THP compositions that provide a minimal lag time, similar to that of an IR THP product, provide extended release with minimal or no initial burst release, and maintain a stable therapeutic plasma concentration of the drug for extended periods of time. There remains a need in the art for ER THP compositions that provide extended release of THP with minimal lag time of about 30 minutes or less. There remains a need in the art for ER THP compositions containing an IR drug layer to minimize the lag time, and an ER portion to provide membrane-controlled extended release with minimal or no initial burst release of the drug beyond the therapeutic range. There remains a need in the art for ER THP compositions that will allow for reduced frequency of administration of the composition, improve patient compliance, provide consistent plasma levels by improving drug solubility at a pH of greater than or equal to about 5, and reduce side effects associated with an unwanted initial burst in drug release; and for development of once-a-day ER THP compositions that can provide a lag time of about 30 minutes or less, provide an extended release for at least about 16 hours (preferably about 24 hours), and reduce side effects associated with initial burst release of the drug.

4. SUMMARY

The present disclosure provides a pharmaceutical pellet composition comprising a core comprising an organic acid; a first drug layer encompassing at least a portion of the core, wherein the first drug layer comprises trihexyphenidyl hydrochloride; and a functional coat encompassing the drug layer, wherein the functional coat comprises a nonionic water-insoluble polymer and a pore former. In certain embodiments, the first drug layer comprises from about 1 mg to about 10 mg of trihexyphenidyl hydrochloride. In certain embodiments, the composition provides extended release of trihexyphenidyl hydrochloride, with a $C_{min}:C_{max}$ ratio of ≥0.4 for a period of at least about 12 hours. In certain embodiments, the composition improves solubility of THP hydrochloride at a pH of greater than or equal to about 5 to maintain a therapeutic concentration for at least about 12 hours.

In certain embodiments, the composition maintains the therapeutic concentration of trihexyphenidyl hydrochloride for a period of at least about 16 hours.

In certain embodiments, the composition of the present disclosure maintains the concentration of trihexyphenidyl hydrochloride in plasma from about 1 ng/ml to about 20 ng/ml for a period of at least about 12 hours. In other embodiments, the composition of the present disclosure maintains the concentration of trihexyphenidyl hydrochloride in plasma from about 1 ng/ml to about 20 ng/ml for a period of at least about 16 hours.

In certain embodiments, the core consists of one or more organic acids.

In certain embodiments, the core comprises organic acid and microcrystalline cellulose.

In certain embodiments, the core is a microcrystalline cellulose sphere coated with an organic acid layer.

In certain embodiments, the organic acid is selected from the group comprising tartaric acid, citric acid, fumaric acid, succinic acid, malic acid, and combinations thereof.

In certain embodiments, the organic acid is tartaric acid.

In certain embodiments, the drug layer further comprises a nonionic water-soluble polymer that is methyl cellulose and/or hydroxypropyl methylcellulose.

In certain embodiments, the nonionic water-insoluble polymer in the functional coat is selected from the group consisting of ethyl cellulose, cellulose acetate, a polyvinyl acetate dispersion, and combinations thereof.

In certain embodiments, the pore former in the functional coat is an enteric polymer selected from the group consisting of cellulose acetate phthalate, cellulose acetate succinate, methylcellulose phthalate, hydroxyethyl cellulose phthalate, polyvinyl acetate phthalate, polyvinyl butyrate acetate, vinyl acetate-maleic anhydride copolymer, methacrylic acid copolymer, hydroxypropyl methylcellulose phthalate, polyvinyl acetate phthalate, cellulose acetyl phthalate, and combinations thereof.

In certain embodiments, the pore former in the functional coat is a nonionic water-soluble polymer comprising methyl cellulose, hydroxypropyl cellulose, hydroxypropyl methylcellulose, polyethylene glycol, or mixtures thereof.

In certain embodiments, the nonionic water-insoluble polymer in the functional coat is ethyl cellulose and the enteric polymer in the functional coat is hydroxypropyl methylcellulose phthalate.

In certain embodiments, the present disclosure provides for a composition comprising a core comprising an organic acid; a first drug layer encompassing at least a portion of the core, wherein the first drug layer comprises trihexyphenidyl hydrochloride; a functional coat encompassing the drug layer, wherein the functional coat comprises a nonionic water-insoluble polymer and a pore former, and a second drug layer comprising trihexyphenidyl hydrochloride. In certain embodiments, the second drug layer further comprises an organic acid.

The present disclosure also provides for a therapeutic method for treating dystonia, sialorrhea, or dyskinesia, the method comprising orally administering to a subject in need thereof an extended release trihexyphenidyl hydrochloride composition, wherein the composition comprises a core comprising an organic acid; a first drug layer encompassing the core, wherein the drug layer comprises trihexyphenidyl hydrochloride; and a functional coat encompassing the drug layer, wherein the functional coat comprises a nonionic water-insoluble polymer and a pore former, wherein the composition provides extended release of trihexyphenidyl hydrochloride, with a $C_{min}:C_{max}$ ratio of ≥0.4, for a period of at least about 12 hours, and wherein the composition improves solubility of trihexyphenidyl hydrochloride at a pH of greater than or equal to about 5 to maintain a therapeutic concentration for at least about 12 hours. In certain embodiments, the composition is administered once a day. In certain embodiments, the composition of the present disclosure can maintain the concentration of trihexyphenidyl hydrochloride in plasma is from about 1 ng/ml to about 20 ng/ml.

The present disclosure also provides a method for improving patient compliance, the method comprising orally administering to a subject in need thereof an extended release trihexyphenidyl hydrochloride composition, wherein the composition improves solubility of trihexyphenidyl hydrochloride at a pH of greater than or equal to about 5 to maintain a therapeutically effective concentration of trihexyphenidyl hydrochloride for a period of at least about 12 hours, and wherein the composition reduces side effects associated with high peak serum concentration ($C_{max}$) and low trough-to-peak concentration ratios ($C_{min}$:$C_{max}$) of <0.4.

In certain embodiments, the side effects include drowsiness, dizziness or blurred vision, dry mouth, stomach upset, vomiting, diarrhea, constipation, and difficulty in urinating.

In certain embodiments, the disclosure provides a composition for providing extended release of trihexyphenidyl hydrochloride for a period of about 12 hours to about 24 hours, wherein the composition solubilizes trihexyphenidyl hydrochloride at a pH of greater than or equal to about 5.

5. BRIEF DESCRIPTION OF THE DRAWINGS

FIG. 1 compares kinetic solubility of trihexyphenidyl hydrochloride (API control (Ctrl)) and trihexyphenidyl hydrochloride-tartaric acid pellets at different drug: tartaric acid ratios (as represented by various percentages of drug layering), performed using USP Apparatus I at 100 RPM and 37° C., in 900 ml of pH 6.8 phosphate buffer.

Figure 2:
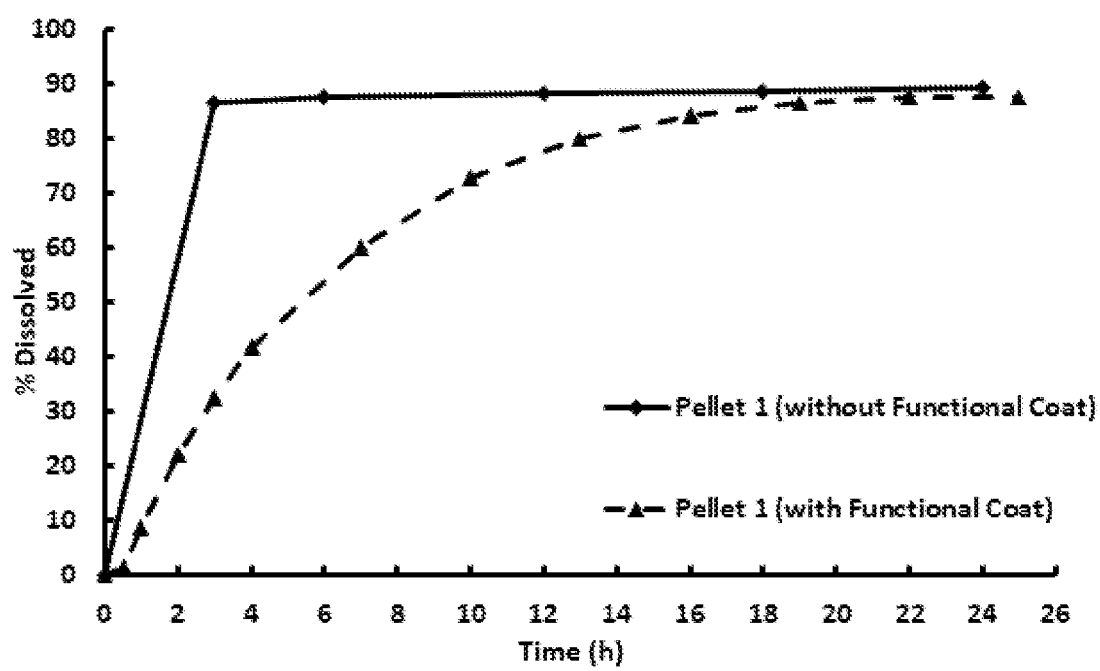

FIG. 2 compares two-stage dissolution profiles of trihexyphenidyl hydrochloride pellets of the disclosure (Pellet 1 with a core comprising tartaric acid, seal coat, drug layer, and functional coat; and Pellet 1 with a core comprising tartaric acid, seal coat, and drug layer, but without a functional coat), performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. FIG. 2 demonstrates that the THP Pellet without a functional coat exhibits faster dissolution compared to the THP Pellet with a functional coat.

Figure 3:
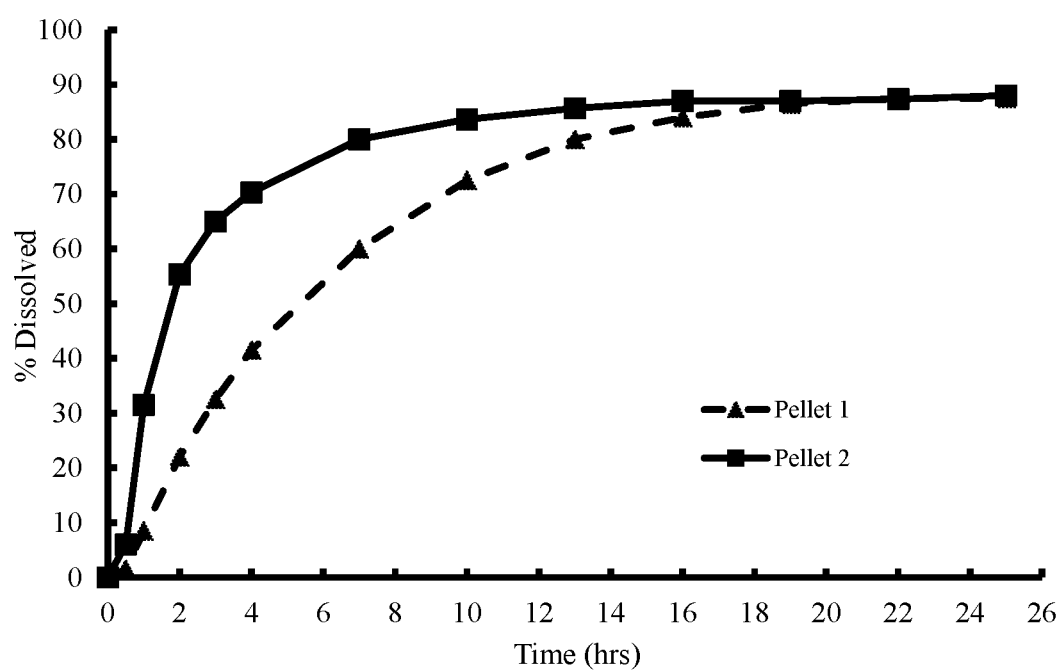

FIG. 3 compares two-stage dissolution profiles of trihexyphenidyl hydrochloride Pellet 1 (containing 50 mg tartaric acid) and Pellet 2 (containing 200 mg tartaric acid), Performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. FIG. 3 demonstrates that Pellet 2 containing 200 mg tartaric acid, exhibits faster dissolution compared to Pellet 1 containing 50 mg tartaric acid.

Figure 4:
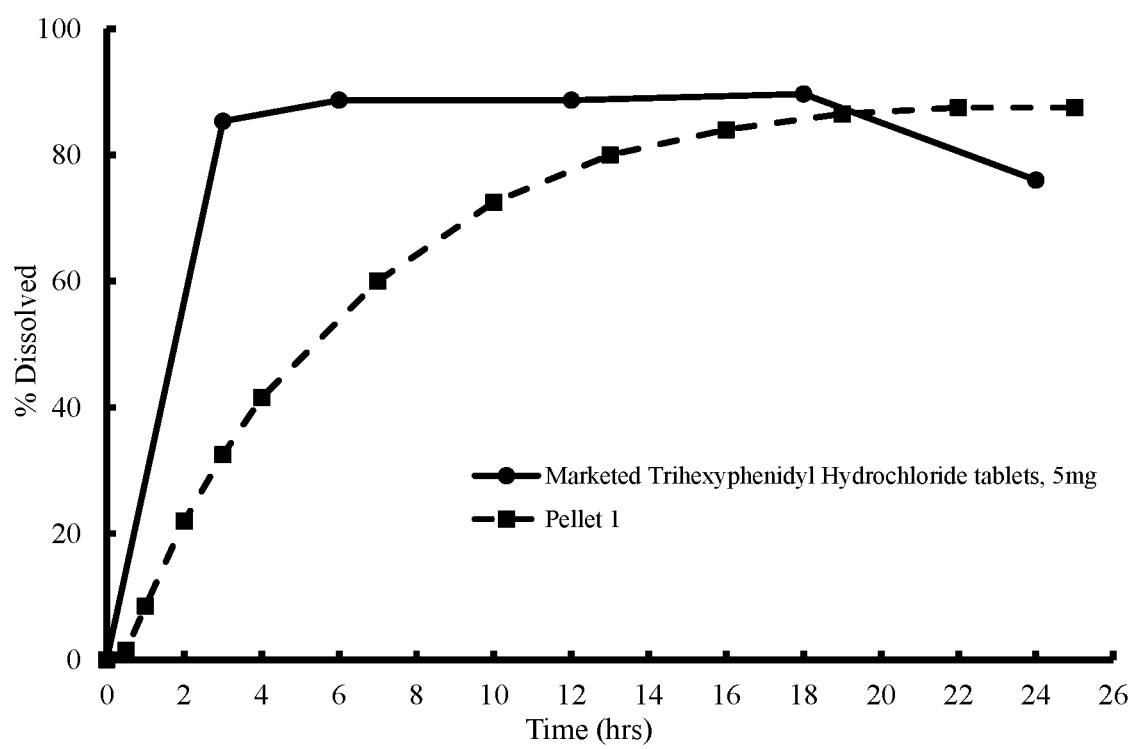

FIG. 4 compares trihexyphenidyl release profiles from Pellet 1 and marketed trihexyphenidyl hydrochloride tablets (5 mg), performed using USP Apparatus I at 100 RPM and 37° C., in 900 ml of pH 6.8 phosphate buffer for 24 hours. FIG. 4 demonstrates that the marketed product provides rapid and uncontrolled release compared to Pellet 1.

Figure 5:
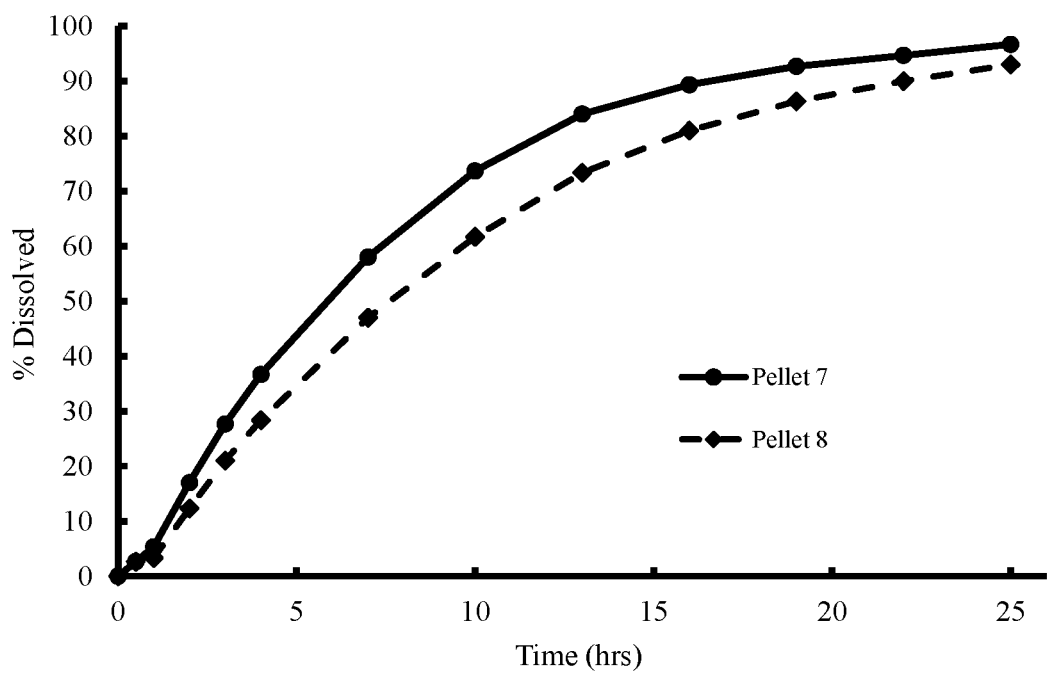

FIG. 5 compares two-stage dissolution profiles of trihexyphenidyl hydrochloride Pellet 7 with 20% functional coating weight gain with respect to the drug layered tablet, and Pellet 8 with 25% functional coating weight gain with respect to the drug layered tablet, performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions.

Figure 6:
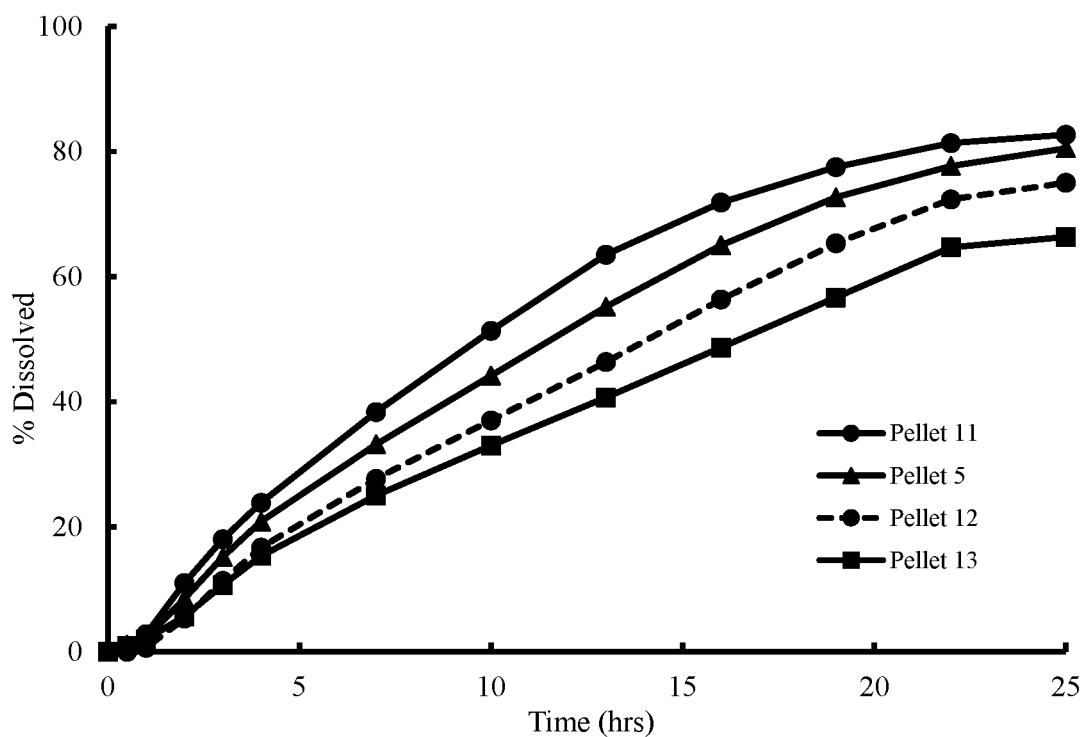

FIG. 6 compares two-stage dissolution profiles for trihexyphenidyl hydrochloride Pellets 5, 11, 12, and 13 containing 25%, 20%, 30%, and 35% coating weight gain in the functional coat, respectively, and performed using USP Apparatus I at 100 RPM and 37° C., in 900 ml of pH 1.2 HCl for 1 hour followed by dissolution in 900 ml of pH 6.8 phosphate buffer for 24 hours, to simulate physiological conditions. FIG. 6 demonstrates that the release rate increases with decreasing functional coat weight gain. Pellets with 20% wt gain of the functional coat show the fastest release rate, and pellets with 35% wt gain of the functional coat show the slowest release rate.

Figure 7:
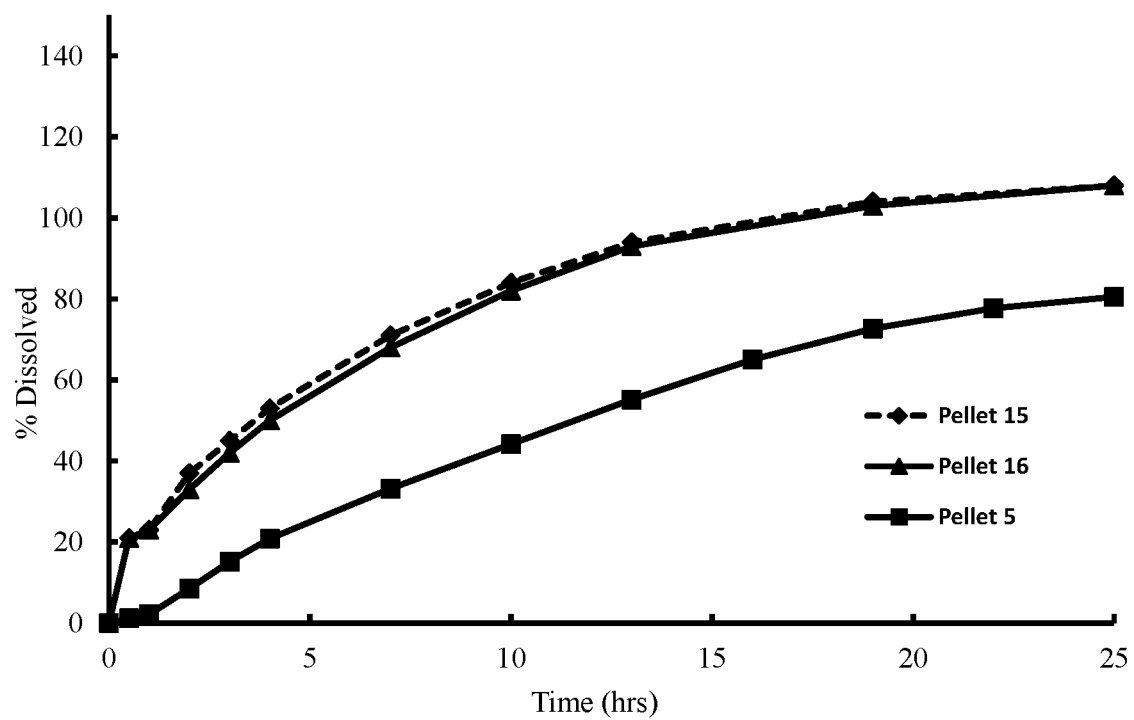

FIG. 7 compares two-stage dissolution profiles of trihexyphenidyl hydrochloride Pellets 5, 15, and 16, performed using USP Apparatus I at 100 RPM and 37° C., in 900 ml of pH 1.2 HCl for 1 hour followed by dissolution in 900 ml of pH 6.8 phosphate buffer for 24 hours, to simulate physiological conditions. FIG. 7 demonstrates that Pellet 5 (without IR drug layer-2) exhibits a lag time of about 2 hours, and Pellets 15 and 16 (containing drug layer-2) do not. FIG. 7 further demonstrates that Pellets 15 and 16 provide better drug recovery compared to Pellet 5 (without an IR drug layer).

Figure 8:
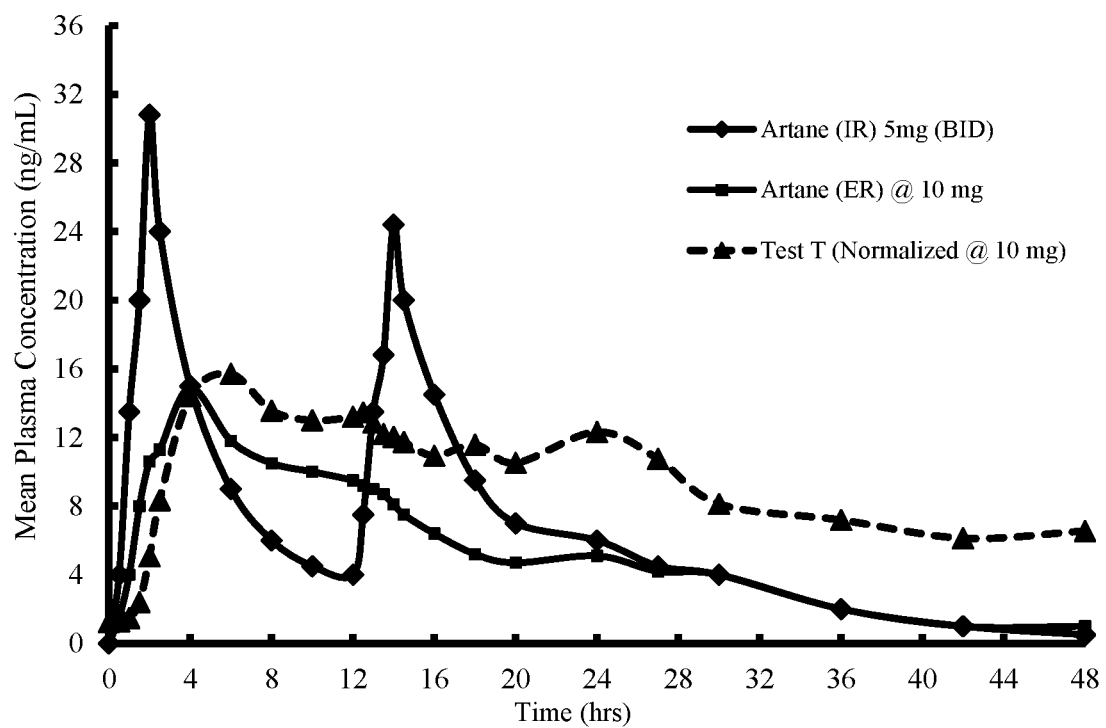

FIG. 8 compares pharmacokinetic data for Artane IR (5 mg BID), and Artane ER (10 mg QD) (see, Cheung et al. (1988), supra) with a 5 mg extended release composition of the disclosure (Test T) (normalized at 10 mg). FIG. 8 demonstrates that Test T exhibits reduced variability in plasma concentration of THP over an extended time period compared to Artane IR (5 mg BID) and Artane ER (10 mg QD).

Figure 9:
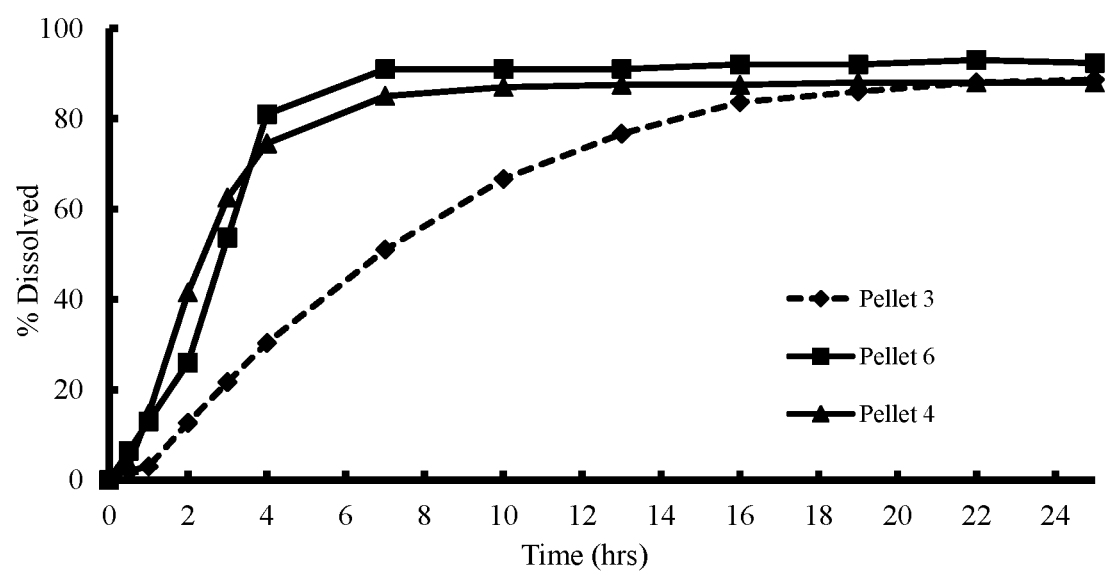

FIG. 9 compares a two-stage dissolution profile of Pellets 3, 4, and 6, performed using USP Apparatus I at 100 RPM and 37° C., in 900 ml of pH 1.2 HCl for 1 hour followed by dissolution in 900 ml of pH 6.8 phosphate buffer for 24 hours. FIG. 9 demonstrates that Pellet 3, containing ethyl cellulose and hypromellose phthalate (HP 55), provides better controlled release of the drug compared to Pellet 4, containing ethyl cellulose and hypromellose (Methocel E5 Prem LV), and Pellet 6 containing Eudragit 5100 and hypromellose phthalate (HP 55) in the functional coat.

6. DETAILED DESCRIPTION

The presently disclosed subject matter provides ER trihexyphenidyl hydrochloride (THP HCl) compositions suitable for once- or twice-daily administration. The ER compositions of the disclosure reduce drug toxicity and drug-related side effects, compared to IR THP tablets, by reducing peak serum concentration ($C_{max}$) and increasing trough-to-peak ratios ($C_{min}$:$C_{max}$) of THP HCl, and provide consistent plasma levels by improving drug solubility at pH of greater than or equal to about 5.

The compositions of the disclosure provide membrane-controlled extended release of THP HCl, wherein the membrane controls the drug release in the stomach and extends the release of the drug in lower regions of the gastrointestinal (GI) tract with a pH greater than or equal to about 5. The compositions of the disclosure provide an acid microenvironment within the dosage form to improve the solubility of THP HCl in regions of the GI tract with a pH greater than or equal to about 5. The membrane-controlled extended release and the presence of an acid microenvironment to improve solubility provide and maintain a minimum therapeutic plasma concentration, without an initial burst release/dose dumping, of THP HCl. The ER THP HCl compositions of the disclosure include pellets suitable for dosing in capsules, sachets, and as sprinkles on food. In certain embodiments, the compositions of the disclosure provide extended release of THP HCl for at least about 16 hours, e.g., about 24 hours. In certain embodiments, the disclosure provides methods for making ER pellets of THP HCl. In certain embodiments, the disclosure provides methods for making trihexyphenidyl capsules containing extended release THP HCl pellets. In certain embodiments, the disclosure provides methods of treating all forms of parkinsonism, e.g., postencephalitic, arteriosclerotic, and idiopathic parkinsonism, using extended release THP HCl pellets. In certain embodiments, trihexyphenidyl hydrochloride pellets of the disclosure are used as adjuvant therapy with levodopa when treating the above-mentioned forms of parkinsonism. In certain embodiments, the disclosure provides methods for treating primary dystonia, dystonia associated with cerebral palsy (dyskinetic cerebral palsy), and/or sialorrhea, using extended release THP HCl pellets. In certain embodiments, the THP HCl pellets of the disclosure are used for controlling extrapyramidal disorders caused by central nervous system drugs such as dibenzoxazepines, phenothiazines, thioxanthenes, and butyrophenones.

For clarity and not by way of limitation, this detailed description is divided into the following subportions:
- 6.1. Definitions;
- 6.2. Formulations of Pellet Dosage Forms;
- 6.3. Compositions;
- 6.4. Methods of Making; and
- 6.5. Methods of Use.

6.1. Definitions

The terminology used in the present disclosure is for the purpose of describing particular embodiments only and is not intended to be limiting. As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

As used herein, "and/or" refers to and encompasses any and all possible combinations of one or more of the associated listed items. The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 15%, up to 10%, up to 5%, up to 1%, up to 0.5%, or even up to 0.1% of a given value. Unless otherwise defined, all terms, including technical and scientific terms used in the description, have the same meaning as commonly understood by one of ordinary skill in the art to which this disclosure belongs. As used herein, "about" will be understood by persons of ordinary skill in the art and will vary to some extent on the context in which it is used. If there are uses of the term which are not clear to persons of ordinary skill in the art given the context in which it is used, "about" will mean up to ±10% of the particular term.

The term "burst release," as used herein, refers to release of THP or a salt thereof in an amount that is outside (i.e., above) the therapeutic range, and providing a drug plasma concentration level that can result in various unwanted side effects.

As used herein, the terms "drug layer-1" and "first drug layer" are used interchangeably and refer to a layer comprising THP that is located closer to the core than the second drug layer and provides extended release of THP. Likewise, as used herein, the terms "drug layer-2" and "second drug layer" are used interchangeably and refer to a layer comprising THP that is located further from the core than the first drug layer, and provides immediate release of THP. In certain embodiments in which only one drug layer is present, that drug layer will be drug layer-1.

As used herein, the terms "extended release" and "sustained release" are used interchangeably and refer to dosage forms or compositions that are formulated to maintain relatively consistent drug concentrations in plasma during a dosing interval comprising an extended period of time (i.e., post-administration), as compared to the drug administered as an immediate release dosage form.

The term "gastric fluid," as used herein, refers to medium occurring in the stomach of an individual.

The term "immediate release," as used herein, refers to release of at least 70% of a drug in about one hour (i.e., post-administration).

The term "permeable," as used herein, refers to a membrane containing sparingly soluble polymers, or insoluble polymers, with or without a pore former(s) that will allow particles/fluids to pass through membrane by diffusion. As used herein, the terms functional coat and permeable membrane are used interchangeably.

The terms "pore former" and the like, as used herein, refer to pH-dependent or pH-independent water-soluble polymers and/or water-soluble small molecules that will form pores or channels (i.e., behave as a channeling agent) in the functional coat, thereby creating a permeable functional coat/membrane. The term "pore former" includes molecules used to create a certain amount of diffusion through an insoluble coating of a tablet, pellet, or particle to achieve a sustained release profile. In certain embodiments, the pore former includes enteric polymers.

The term "simulated gastric fluid," as used herein, refers to a medium that is used to mimic the chemical environment of gastric medium in an in vitro setting.

The term "substantially free," as used herein, means that the composition comprises less than 0.001 wt % of the material.

As used herein, the term "therapeutic concentration" refers to a plasma concentration of THP between about 1 ng/ml and about 20 ng/ml for THP compositions, based on the strength of the dosage form.

As used herein, a "therapeutically effective," "pharmaceutically acceptable," or "therapeutically acceptable" amount refers to an amount that will elicit a therapeutically useful response in a subject and includes an additional amount or overage of active ingredient deemed necessary in the formulation to provide the desired amount upon administration. The therapeutically useful response can provide some alleviation, mitigation, and/or decrease in at least one clinical symptom in the subject. Those skilled in the art will appreciate that the therapeutically useful response need not be complete or curative, as long as some benefit is provided to the subject. In some embodiments, the subject is a human. In certain embodiments, a "therapeutically effective," "pharmaceutically acceptable," or "therapeutically acceptable" amount refers to a dose that produces a plasma level of THP between about 1 ng/ml and about 20 ng/ml for THP compositions, based on the strength of the dosage form.

As used herein, the terms "treatment," "treat," and "treating" refer to reversing, alleviating, delaying the onset of, and/or inhibiting the progress of a disease or disorder as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example to prevent or delay their recurrence.

As used herein, the terms "trihexyphenidyl" and "trihexyphenidyl hydrochloride" are used interchangeably herein. The term "trihexyphenidyl" includes all pharmaceutically acceptable salts, esters, and functionally equivalent chemical compounds, including trihexyphenidyl hydrochloride.

As used herein, the terms "up," "down," "above," "below," "top," "bottom," etc. should be interpreted as nonlimiting upon the pellets, cores, layers, methods, and products of any methods of present disclosure, which can be spatially arranged in any orientation or manner.

6.2. Formulations of Pellet Dosage Forms

The present disclosure provides extended release oral trihexyphenidyl hydrochloride drug compositions that maintain solubility of the drug in different pH environments of the GI tract, and maintain a therapeutic plasma concentration of the drug for extended periods of time, without an initial spike or burst in release of the drug. Trihexyphenidyl is an anticholinergic agent. It exerts a direct inhibitory effect upon the parasympathetic nervous system. It also has a relaxing effect on smooth musculature.

Trihexyphenidyl is commonly prescribed as trihexyphenidyl hydrochloride. However, use of other pharmaceutically acceptable salts of trihexyphenidyl is also contemplated in the present disclosure.

Pharmaceutically acceptable salts of trihexyphenidyl known in the art include, but are not limited to, hydrochloride, hydrobromide, hydroiodide, bromide, sulfite, sulfate, bisulfate, nitrate, salicylate, citrate, tartrate, bitartrate, lactate, phosphate, malate, maleate, fumarate, succinate, acetate, and pamoate salts.

In certain embodiments, the present disclosure provides for compositions that comprise THP and are able to maintain plasma concentrations of THP above 80% of $C_{max}$ for an average time period of about 6 hours, above 70% of $C_{max}$ for an average time period of about 8 hours, above 60% of $C_{max}$ for an average time period of about 12 hours, and above 50% of $C_{max}$ value for an average time period of about 24 hours post-administration of the extended release THP composition, compared with values of about 80% of $C_{max}$ at 3 hours, about 70% of $C_{max}$ at 4 hours, and about 30% $C_{max}$ at about 8 hours post-administration of an immediate release THP composition.

In certain embodiments, compositions of the present disclosure comprise THP extended release pellets. In certain embodiments, the compositions described herein comprise capsules containing extended release pellets. In certain embodiments, the extended release pellets comprise a core coated with a seal coat, a drug layer over the seal coat, and a functional coat/membrane over the drug-layered core. In certain embodiments, the core is a nonpareil seed (e.g., cellet, sugar sphere) layered with an organic acid. In certain embodiments, the compositions of the disclosure comprise an additional drug layer (drug layer-2) over the functional coat. In certain embodiments, the compositions of the present disclosure comprise a seal coat between the functional coat and the drug layer-2. In certain embodiments, the compositions of the disclosure comprise an over coat over drug layer-2. Each component of the compositions of the present disclosure is described in more detail below.

6.2.1. Core

In certain embodiments, the present disclosure provides pellets comprising a core that comprises an organic acid. The organic acid in the core provides an acidic microenvironment to increase solubility of trihexyphenidyl, which is a weak base with poor solubility at a pH of greater than or equal to about 5. In certain embodiments, the core is spherical or irregular in shape. In certain embodiments, the core comprises an organic acid. In a specific embodiment, the core consists of an organic acid. In certain embodiments, the core is a nonpareil seed coated with an organic acid, e.g., a cellet/sugar sphere coated with an organic acid. In certain embodiments, the core is a microcrystalline cellulose sphere coated with an organic acid. In certain embodiments, the organic acid coat over the nonpareil seed contains trihexyphenidyl. In certain embodiments, the core is coated with a coat containing trihexyphenidyl hydrochloride and additional organic acid. In certain embodiments, the additional organic acid in the coating can be same as the organic acid present in the core. In certain embodiments, the additional organic acid in the coating can be different from the organic acid present in the core.

In certain embodiments, the organic acid in the core is capable of protonating trihexyphenidyl present in the pellet. As protonated trihexyphenidyl is more soluble than trihexyphenidyl free base, a greater absorption of the active ingredient is provided. In certain embodiments, the organic acid in the core improves in vivo solubility of trihexyphenidyl. In certain embodiments, the organic acid in the core improves absorption of, and increases the plasma levels of, THP. In certain embodiments, the compositions of the present disclosure provide for a higher solubility of trihexyphenidyl hydrochloride at a pH of greater than or equal to about 5 and can maintain a therapeutically effective plasma concentration of trihexyphenidyl for extended time periods.

Without being bound to any particular theory, the organic acid in the core is believed to enhance the dissolution and absorption of trihexyphenidyl in the GI tract. The organic acid in the core solubilizes and lowers the microenvironmental pH of the pellet. As the microenvironmental pH of the pellet drops, the trihexyphenidyl is protonated and solubilized for absorption in the GI tract.

In certain embodiments, the organic acid in the core is present in a concentration of from about 10% to about 100%, from about 20% to about 80%, from about 30% to about 70% w/w, or any intermediate values thereof, of the core. In certain embodiments, the core consists of one or more organic acids. In certain embodiments, the organic acid is present in amount of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% w/w of the core.

In certain embodiments, the core makes up from about 40% to about 99%, from about 50% to about 95%, from about 60% to about 90% w/w, or any intermediate values thereof, of the composition of the present disclosure. In certain embodiments, the core makes up at least about 40%, at least about 45%, at least about 50%, at least about 55%, at least about 60%, at least about 65%, at least about 70%, at least about 75%, at least about 80%, at least about 85%, at least about 90% w/w, at least about 95%, or at least about 99% w/w of the composition of the present disclosure.

In certain embodiments, the ratio of trihexyphenidyl hydrochloride to organic acid in the core is between about 0.01 (1:100) and about 0.1 (1:10), between about 0.025 (1:40) and about 0.075 (1:13), or about 0.05 (1:20) by weight. In certain embodiments, the ratio of trihexyphenidyl hydrochloride to organic acid in the core is about 1:100, about 1:90, about 1:80, about 1:70, about 1:60, about 1:50, about 1:40, about 1:30, about 1:29, about 1:28, about 1:27, about 1:26, about 1:25, about 1:24, about 1:23, about 1:22, about 1:21, about 1:20, about 1:19, about 1:18, about 1:17, about 1:16, about 1:15, about 1:14, about 1:13, about 1:12, about 1:11, about 1:10, or any intermediate ratios thereof.

In certain embodiments, the organic acid is one or more of tartaric acid, citric acid, fumaric acid, succinic acid, malic acid, or any combinations thereof. In certain embodiments, the organic acid is crystalline tartaric acid.

In certain embodiments, the dosage forms of the present disclosure provide excellent stability and bioavailability of trihexyphenidyl hydrochloride for extended periods of time. The excellent stability and bioavailability of trihexyphenidyl hydrochloride is at least in part provided by the presence of an organic acid that ensures trihexyphenidyl remains solubilized for extended periods of time after oral administration, even in a weakly acidic, neutral, or basic environment.

6.2.2. Seal Coats and Over Coat

In certain embodiments, the core is coated with a seal coat. In certain embodiments, the seal coat is optional. In certain embodiments, the compositions of the disclosure can include two seal coats (the first one between the core and drug layer-1, and the second one between the functional coat and drug layer-2). In certain embodiments, the compositions of the disclosure include an over coat. In certain embodiments, the compositions of the disclosure include various components and coats in the following order: a core; seal coat-1 over the core; drug layer-1, containing THP for extended release, over seal coat-1; a functional coat over drug layer-1; seal coat-2 over the functional coat; drug layer-2, containing THP for immediate release, over seal coat-2; and an over coat.

In certain embodiments, the seal coat(s) and over coat comprise a nonionic water-soluble polymer. In certain embodiments, the nonionic water-soluble polymer is a cellulose ether polymer selected from a group comprising hydroxypropyl cellulose, methyl cellulose, hydroxypropyl methylcellulose, and mixtures thereof. In certain embodiments, the amount of the polymer ranges from about 5% to about 100% w/w of the seal coat/over coat composition. In certain embodiments, the amount of the polymer ranges from about 10% to about 95%, from about 15% to about 90%, from about 20% to about 85%, from about 25% to about 80%, from about 30% to about 75%, from about 35% to about 70%, from about 40% to about 65%, from about 45% to about 60%, or from about 50% to about 55% w/w of the total weight of the seal coat/over coat composition. In certain embodiments, the polymer is present in an amount of about 70%, about 71%, about 72%, about 73%, about 74%, about 75%, about 76%, about 77%, about 78%, about 79%, about 80% w/w of the seal coat/over coat composition.

In certain embodiments, the composition of the seal coat/over coat further comprises additional excipients, such as anti-tacking agents and/or plasticizers. In certain embodiments, anti-tacking agents include, but are not limited to, silicon dioxide (SYLOID® 244FP), fumed silica (CAB-O-SIL®), talc, kaolin, magnesium trisilicate, powdered starch, tribasic calcium phosphate, and any combinations thereof. In certain embodiments, the anti-tacking agent can be present in an amount of from about 5% to about 30% w/w of the nonionic water-soluble polymer. In certain embodiments, the anti-tacking agent is present in an amount of about 5%, about 10%, about 15%, about 20%, about 25%, about 30% w/w, or any intermediate values therein, by weight of the nonionic water-soluble polymer. In certain embodiments, the plasticizers include, but are not limited to, glycerin, polyethylene glycol monomethyl ether, triethyl citrate, triacetin, polyethylene glycol, propylene glycol, sorbitol sorbitan solution, dibutyl sebacate, or mixtures thereof. In certain embodiments, the plasticizer is triethyl citrate. In certain embodiments, the plasticizer is dibutyl sebacate. In certain embodiments, the plasticizer is present in an amount of about 0.1%, about 1%, about 2%, about 3%, about 4%, about 5%, about 6%, about 7%, about 8%, about 9%, about 10% w/w, or any intermediate values therein, of the nonionic water-soluble polymer. In certain embodiments, the seal coat/over coat is substantially free of a plasticizer. In certain embodiments, the amount of the additional excipients, when present, can range from about 0.1% to about 40%, from about 1% to about 35%, from about 2% to about 30%, from about 3% to about 25%, or from about 4% to about 20% w/w, of the total weight of the nonionic water-soluble polymer, and in some embodiments from about 0.5% to about 25% w/w of the nonionic water-soluble polymer. In certain embodiments, the additional excipients are present in amount of at least about 1%, at least about 5%, at least about 10%, at least about 15%, at least about 20%, at least about 25%, or at least about 30% w/w, of the total weight of the nonionic water-soluble polymer.

6.2.3. Drug Layer

In certain embodiments, the core (uncoated core, core coated with a seal coat, nonpareil seed coated with an organic acid, and nonpareil seed coated with an organic acid and a seal coat) is further coated with a drug layer. In certain embodiments, the drug layer comprises trihexyphenidyl hydrochloride and a nonionic water-soluble polymer. In certain embodiments, the drug layer further comprises at least one organic acid. In certain embodiments, the organic acid includes, but is not limited to, tartaric acid, citric acid, fumaric acid, succinic acid, malic acid, and combinations thereof.

In certain embodiments, the compositions of the disclosure comprise a first drug layer, which is an extended release drug layer (drug layer-1) and a second drug layer, which is an immediate release drug layer (drug layer-2). In certain embodiments, the ratio of trihexyphenidyl hydrochloride in the extended release portion and the immediate release drug layer-2 is between about 70:30 and about 100:0. In certain embodiments, the ratio of trihexyphenidyl hydrochloride in the extended release portion and the immediate release portion is about 70:30, about 75:25, about 80:20, about 85:15, about 90:10, about 95:5, about 100:0, or any intermediate ratios therein. In certain embodiments, drug layer-1 is between seal coat-1 and the functional coat. In certain embodiments, the functional coat controls the release of trihexyphenidyl hydrochloride from drug layer-1. In certain embodiments, drug layer-2 is between seal coat-2 and the over coat.

In certain embodiments, the trihexyphenidyl hydrochloride is present in a concentration of from about 10% to about 70%, from about 15% to about 65%, from about 20% to about 60%, from about 25% to about 55%, or from about 30% to about 50% by weight of the drug layer (drug layer-1 and drug layer-2) composition. In certain embodiments trihexyphenidyl hydrochloride is present in a concentration of about 30%, about 35%, about 40%, about 45%, about 50%, about 51%, about 52%, about 53%, about 54%, about 55%, about 56%, about 57%, about 58%, about 59%, or about 60% w/w of the drug layer composition. In certain embodiments, trihexyphenidyl hydrochloride is present in a concentration of between about 1% w/w and about 10% w/w, based on the total weight of the composition.

In certain embodiments, the nonionic water-soluble polymer that can be included in the drug layer (drug layer-1 and/or drug layer-2) is a cellulose ether polymer (e.g., a water-soluble methylcellulose and/or hydroxypropyl methylcellulose polymer). In certain embodiments, the amount of the polymer ranges from about 5% to about 95%, from about 10% to about 90%, about 20% to about 80%, from about 30% to about 70%, from about 40% to about 60%, or from about 45% to about 55% w/w of the total weight of the drug layer composition. In certain embodiments, the concentration of the polymer ranges from about 10% to about 40%, e.g., about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, and about 39% w/w, or intermediate values thereof, of the drug layer composition.

In certain embodiments, the drug layer(s) further includes additional excipients comprising anti-tacking agents, and/or plasticizers. In certain embodiments, anti-tacking agents include, but are not limited to, silicon dioxide (SYLOID® 244FP), fumed silica (CAB-O-SIL®), talc, kaolin, magnesium trisilicate, powdered starch, and/or tribasic calcium phosphate. In certain embodiments, the anti-tacking agent can be present in an amount of about 5% to about 100% w/w of the polymer present in the drug layer(s). In certain embodiments, the anti-tacking agent is present in an amount of about 10% w/w, about 20% w/w, about 30% w/w, about 40% w/w, about 50% w/w, about 60% w/w, about 70% w/w, about 80% w/w, or about 90% w/w of the polymer present in the drug layer(s). In certain embodiments, the plasticizers include, but are not limited to, glycerin, triethyl citrate, triacetin, polyethylene glycol, propylene glycol, sorbitol sorbitan solution, and/or dibutyl sebacate. In certain embodiments, the plasticizer is triethyl citrate. In certain embodiments, the plasticizer is dibutyl sebacate. In certain embodiments, the plasticizer is present in an amount of about 0.1%, about 1%, about 2%, about 3%, about 4%, about 5%, about 6%, about 7%, about 8%, about 9%, about 10% w/w, or any intermediate values therein, of nonionic water-soluble polymer. In certain embodiments, the total amount of the additional excipients is present in a range from about 0.1% to about 100%, from about 1% to about 50%, from about 2% to about 40%, from about 3% to about 35%, from about 4% to about 30%, from about 5% to about 25%, or from about 6% to about 20% w/w of the nonionic water-soluble polymer.

In certain embodiments, the drug layer (e.g., drug layer-1 and/or drug layer-2) comprise at least one organic acid to solubilize trihexyphenidyl. In certain embodiments, the immediate release drug layer, e.g., drug layer-2, comprises at least one organic acid. In certain embodiments, drug layer-1 (extended release drug layer) does not require any organic acid as the drug layer is in close proximity to a core comprising organic acid. In certain embodiments, drug layer-1 does not comprise an organic acid, and drug layer-2 comprises an organic acid. In certain embodiments, the organic acid comprises tartaric acid, citric acid, fumaric acid, succinic acid, malic acid, or any combinations thereof. In certain embodiments, the organic acid in drug layer-2 is different from the organic acid in the core. In certain embodiments, the organic acid in the core is tartaric acid and the organic acid in drug layer-2 is succinic acid. In certain embodiments, the organic acid in the core and drug layer-2 is tartaric acid or succinic acid.

6.2.4. Functional Coat/Extended Release Layer/Membrane

In certain embodiments, the drug-layered pellet is further coated with a functional coat. In certain embodiments, there is a seal coat between the drug layer (drug layer-1) and the functional coat. In certain embodiments, the functional coat covers at least a portion of the drug layer (e.g., drug layer-1). In certain embodiments, the functional coat is positioned between drug layer-1 and seal coat-2. In certain embodiments, the functional coated pellet is cured by heating the functional coated pellet for between about 30 minutes and about 2 hours, at a temperature of between about 20° C. and about 45° C., e.g., between about 20° C. and about 30° C.

In certain embodiments, the functional coat comprises at least one water-insoluble polymer. In certain embodiments, the functional coat further includes a water-soluble polymer as a pore former. In certain embodiments, the pore former is an enteric polymer. In certain embodiments, the enteric polymer used as a pore former comprises, but is not limited to, cellulose acetate phthalate, cellulose acetate succinate, methylcellulose phthalate, hydroxyethyl cellulose phthalate, polyvinyl acetate phthalate, polyvinyl butyrate acetate, vinyl acetate-maleic anhydride copolymer, hydroxypropyl methylcellulose phthalate, polyvinyl acetate phthalate, cellulose acetyl phthalate, methacrylic acid and methyl methacrylate (1:2) copolymer (EUDRAGIT® S 100), methacrylic acid and methyl methacrylate (1:1) copolymer (EUDRAGIT L®100), methacrylic acid and methyl methacrylate (1:2) copolymer solution (EUDRAGIT® S 12.5), methacrylic acid and methyl methacrylate (1:1) copolymer solution (EUDRAGIT® L 12.5), and combinations thereof. In certain embodiments, the pore former is a nonionic water-soluble polymer comprising, but not limited to, methyl cellulose, hydroxypropyl cellulose, hydroxypropyl methylcellulose, polyethylene glycol, or mixtures thereof.

In certain embodiments, the water-insoluble polymer in the functional coat comprises, but is not limited to, ethyl cellulose (ETHOCEL™), cellulose acetate, a polyvinyl acetate dispersion (KOLLICOAT® SR), or mixtures thereof.

In certain embodiments, the water-insoluble polymer is present in an amount of from about 40% to about 80%, from about 50% to about 70%, from about 55% to about 65%, (e.g., about 60%) w/w, or any intermediate value therein, of the functional coat. In certain embodiments, a pore former is present in an amount of from about 5% to about 50%, from about 10% to about 25%, from about 15% to about 20% w/w, or any intermediate values therein, of the functional coat.

In certain embodiments, the functional coat further comprises at least one plasticizer and at least one anti-tacking agent. Useful anti-tacking agents include, but are not limited to, silicon dioxide (SYLOID® 244FP), fumed silica (CAB-O-SIL®), talc, kaolin, talc, magnesium trisilicate, powdered starch, and/or tribasic calcium phosphate. In certain embodiments, the anti-tacking agent can be present in an amount of from about 5% to about 30% w/w of the combined weight of the water-insoluble polymer and the pore former. In certain embodiments, the anti-tacking agent is present in an amount of about 5%, about 10%, about 15%, about 20%, about 25%, about 30% w/w, or any intermediate values therein, of the combined weight of the water-insoluble polymer and the pore former. In certain embodiments, plasticizers include, but are not limited to, glycerin, polyethylene glycol monomethyl ether, triethyl citrate, triacetin, polyethylene glycol, propylene glycol, sorbitol sorbitan solution, dibutyl sebacate, or mixtures thereof. In certain embodiments, the plasticizer is triethyl citrate. In certain embodiments, the plasticizer is dibutyl sebacate. In certain embodiments, the plasticizer is present in an amount of about 0.1%, about 1%, about 2%, about 3%, about 4%, about 5%, about 6%, about 7%, about 8%, about 9%, about 10% w/w, or any intermediate values therein, of the combined weight of the water-insoluble polymer and the pore former.

In certain embodiments, the range of ratios of water-insoluble polymer to pore former is from about 60:40 to about 99.5:0.5. In certain embodiments, the ratio of water-insoluble polymer to the pore former is about 70:30, about 75:25, about 80:20, about 85:15, about 90:10, about 95:5, or any intermediate ranges therein. In certain embodiments, the functional coat comprises a water-insoluble polymer, a plasticizer, and a pore former. In certain embodiments, the plasticizer acts as a pore former. In certain embodiments, the ratio of water-insoluble polymer and plasticizer determines the release rate of trihexyphenidyl hydrochloride. In certain embodiments, the enteric polymer functions as a pore former to release the trihexyphenidyl hydrochloride flux generated due to the presence of an acid microenvironment in the dosage form. In certain embodiments, (1) the presence of acid microenvironment and (2) the enteric polymer together control the release rate of trihexyphenidyl hydrochloride at a pH of greater than or equal to about 5.

6.2.5. Pellets

In certain embodiments, the present disclosure provides extended release oral trihexyphenidyl hydrochloride drug compositions that maintain solubility of the drug in different pH environments of the GI tract, and maintain a therapeutic plasma concentration of the drug for extended periods of time, without any initial spike or burst in release of the drug.

In certain embodiments, the pellets comprise a core comprising organic acid and coated with a seal coat, a drug layer over the seal coat, and a functional coat/membrane over the drug-layered core. In certain embodiments, the pellets comprise a core coated with seal coat-1, drug layer-1 over seal coat-1, functional coat over drug layer-1, seal coat-2 over functional coat, drug layer-2 over seal coat-2, and an over coat over drug layer-2. In certain embodiments, the pellets comprise a core coated with seal coat-1, drug layer-1 over seal coat-1, and functional coat over drug layer-1.

In certain embodiments, the core comprises from about 10 mg to about 200 mg, from about 20 mg to about 100 mg, from about 30 mg to about 80 mg, from about 40 mg to about 60 mg, or about 50 mg of an organic acid. In particular embodiments, the core comprises from about 10 mg to about 200 mg, from about 20 mg to about 100 mg, from about 30 mg to about 80 mg, from about 40 mg to about 60 mg, or about 50 mg of tartaric acid. In certain embodiments, the core comprises tartaric acid in an amount of from about 45% w/w to about 80% w/w, from about 50% w/w to about 75% w/w, from about 55% w/w to about 70% w/w, or from about 60% w/w to about 65% w/w, based on the total weight of the composition.

In certain embodiments, the seal coat(s) (i.e., seal coat-1 and seal coat-2) and/or the over coat comprise from about 0.1 mg to about 10 mg, from about 0.2 mg to about 9.0 mg, from about 0.3 mg to about 8.0 mg, from about 0.4 mg to about 7.5 mg, from about 0.5 mg to about 7.0 mg, from about 1.0 mg to about 6.0 mg, from about 1.5 mg to about 5.0 mg, from about 2.0 mg to about 4.0 mg, from about 2.5 mg to about 3.5 mg, or about 3.0 mg of hypromellose (METHOCEL® E5 Prem LV). In certain embodiments, the seal coat(s) and/or over coat further comprise from about 0.01 mg to about 0.5 mg, from about 0.02 mg to about 0.4 mg, from about 0.03 mg to about 0.35 mg, from about 0.05 mg to about 0.25 mg, from about 0.06 mg to about 0.20 mg, from about 0.07 mg to about 0.15 mg, or from about 0.08 mg to about 0.10 mg of triethyl citrate. In certain embodiments, the seal coat(s) and/or over coat also comprise from about 0.05 mg to about 2.0 mg, from about 0.1 mg to about 1.5 mg, from about 0.15 mg to about 1.0 mg, from about 0.2 mg to about 0.9 mg, from about 0.25 mg to about 0.8 mg, from about 0.3 mg to about 0.7 mg, from about 0.35 mg to about 0.6 mg, or from about 0.4 mg to about 0.5 mg of talc. In certain embodiments, the seal coat(s) and/or the over coat comprise hypromellose (METHOCEL® E5 Prem LV) in an amount of from about 2.0% w/w to about 5.0% w/w, from about 2.25% w/w to about 4.5% w/w, from about 2.5% w/w to about 4.0% w/w, from about 2.75% w/w to about 3.5% w/w, or from about 3.0% w/w to about 3.25% w/w, based on the total weight of the composition. In certain embodiments, the seal coat(s) and/or over coat further comprise triethyl citrate in an amount of from about 0.05% w/w to about 0.30% w/w, from about 0.06% w/w to about 0.25% w/w, from about 0.07% w/w to about 0.24% w/w, from about 0.08% w/w to about 0.23% w/w, from about 0.09% w/w to about 0.22% w/w, from about 0.10% w/w to about 0.21% w/w, from about 0.11% w/w to about 0.20% w/w, from about 0.12% w/w to about 0.19% w/w, from about 0.13% w/w to about 0.18% w/w, from about 0.14% w/w to about 0.17% w/w, or from about 0.15% w/w to about 0.16% w/w, based on the total weight of the composition. In certain embodiments, the seal coat(s) and/or over coat also comprise talc in an amount of from about 0.5% w/w to about 1.25% w/w, from about 0.55% w/w to about 1.20% w/w, from about 0.60% w/w to about 1.15% w/w, from about 0.65% w/w to about 1.10% w/w, from about 0.70% w/w to about 1.05% w/w, from about 0.75% w/w to about 1.0% w/w, from about 0.80% w/w to about 0.95% w/w, or from about 0.85% w/w to about 0.90% w/w, based on the total weight of the dosage form.

In certain embodiments, drug layer-1 and drug layer-2 comprise trihexyphenidyl hydrochloride, hypromellose, triethyl citrate, and talc. In certain embodiments, drug layer-1 and/or drug layer-2 contain from about 0.5 mg to about 10 mg, from about 1.0 mg to about 9.0 mg, from about 1.5 mg to about 8.5 mg, from about 2.0 mg to about 8.0 mg, from about 2.5 mg to about 7.5 mg, from about 3.0 mg, to about 7.0 mg, from about 3.5 mg to about 6.5 mg, from about 4.0 mg to about 6.0 mg, from about 4.5 mg to about 5.5 mg, or about 5.0 mg of trihexyphenidyl hydrochloride. In certain embodiments, drug layer-1 and/or drug layer-2 comprise from about 0.01 mg to about 6.0 mg, from about 0.5 mg to about 5.0 mg, from about 1.0 mg to about 4.5 mg, from about 1.5 mg to about 4.0 mg, from about 2.0 mg to about 3.5 mg, or from about 2.5 mg to about 3.0 mg of hypromellose. In certain embodiments, drug layer-1 and/or drug layer-2 comprise from about 0.001 mg to about 0.3 mg, from about 0.01 mg to about 0.25 mg, from about 0.05 mg to about 0.2 mg, or from about 0.1 mg to about 0.15 mg of triethyl citrate. In certain embodiments, drug layer-1 and drug layer-2 comprise from about 0.05 mg to about 2.0 mg, from about 0.1 mg to about 1.5 mg, from about 0.2 mg to about 1.45 mg, from about 0.3 mg to about 1.40 mg, from about 0.4 mg to about 1.35 mg, from about 0.5 mg to about 1.30 mg, from about 0.6 mg to about 1.25 mg, from about 0.7 mg to about 1.20 mg, from about 0.8 mg to about 1.15 mg, from about 0.9 mg to about 1.10 mg, or about 1.0 mg of talc. In certain embodiments, total amount of trihexyphenidyl hydrochloride present in drug layer-1 and drug layer-2 is from about 0.5% w/w to about 10% w/w, from about 1.0% w/w to about 9% w/w, from about 1.5% w/w to about 8.0% w/w, from about 2.0% w/w to about 7.0% w/w, from about 2.5% w/w to about 6.5% w/w, from about 3.0% w/w to about 6.0% w/w, from about 3.5% w/w to about 5.5% w/w, from about 4.0% w/w to about 5.0% w/w, or from about 4.5% w/w to about 4.75% w/w, based on the total weight of the composition. In certain embodiments, total amount of hypromellose (METHOCEL® E5 Prem LV) present in drug layer-1 and drug layer-2 is from about 0.05% w/w to about 5.0% w/w, from about 0.10% w/w to about 4.5% w/w, from about 0.15% w/w to about 4.0% w/w, from about 1.0% w/w to about 3.5% w/w, from about 1.25% w/w to about 3.4% w/w, from about 1.5% w/w to about 3.3% w/w, from about 1.75% w/w to about 3.2% w/w, from about 2.0% w/w to about 3.1% w/w, from about 2.25% w/w to about 3.0% w/w, from about 2.5% w/w to about 2.9% w/w, or from about 2.75% w/w to about 2.8% w/w, based on the total weight of the dosage form. In certain embodiments, drug layer-1 and drug layer-2 comprise from about 0.01% w/w to about 0.3% w/w, from about 0.05% w/w to about 0.25% w/w, from about 0.10% w/w to about 0.2% w/w, from about 0.11% w/w to about 0.19% w/w, from about 0.12% w/w to about 0.18% w/w, from about 0.13% w/w to about 0.17% w/w, or from about 0.14% w/w to about 0.16% w/w of triethyl citrate, based on the total weight of the composition. In certain embodiments, drug layer-1 and drug layer-2 comprise from about 0.5% w/w to about 10% w/w, from about 1.0% w/w to about 9% w/w, from about 1.5% w/w to about 8.0% w/w, from about 2.0% w/w to about 7.0% w/w, from about 2.5% w/w to about 6.5% w/w, from about 3.0% w/w to about 6.0% w/w, from about 3.5% w/w to about 5.5% w/w, from about 4.0% w/w to about 5.0% w/w, or from about 4.5% w/w to about 4.75% w/w of talc.

In certain embodiments, the functional coat comprises ethyl cellulose (or Eudragit S 100), hypromellose phthalate (HP 55), triethyl citrate, and talc. In certain embodiments, the functional coat comprises from about 1.0 mg to about 20 mg, from about 2.0 mg to about 19 mg, from about 3.0 mg to about 18 mg, from about 4.0 mg to about 17 mg, from about 5.0 mg to about 16 mg, from about 6.0 mg to about 15 mg, from about 7.0 mg to about 14 mg, from about 8.0 mg to about 13 mg, from about 9.0 mg to about 12, or from about 10 mg to about 11 mg of ethyl cellulose. In certain embodiments, the functional coat comprises from about 0.1 mg to about 5.5 mg, from about 0.5 mg to about 5.0 mg, from about 1.0 mg to about 4.5 mg, from about 1.5 mg to about 4.0 mg, from about 2.0 mg to about 3.5 mg, or from about 2.5 mg to about 3.0 mg of hypromellose phthalate (HP 55). In certain embodiments, the functional coat comprises from about 0.1 mg to about 3.0 mg, from about 0.5 mg to about 2.5 mg, from about 1.0 mg to about 2.0 mg, or from about 1.25 mg to about 1.75 mg of triethyl citrate. In certain embodiments, the functional coat comprises from about 0.1 mg to about 5.5 mg, from about 0.5 mg to about 5.0 mg, from about 1.0 mg to about 4.5 mg, from about 1.5 mg to about 4.0 mg, from about 2.0 mg to about 3.5 mg, or from about 2.5 mg to about 3.0 mg of talc. In certain embodiments, the functional coat comprises ethyl cellulose (or Eudragit S 100), hypromellose phthalate (or Hypromellose/Methocel E5 Prem LV), triethyl citrate, and talc. In certain embodiments, the functional coat comprises from about 8.0% w/w to about 25% w/w, from about 9.0% w/w to about 24% w/w, from about 10% w/w to about 23% w/w, from about 11% w/w to about 22% w/w, from about 12% w/w to about 21% w/w, from about 13% w/w to about 20% w/w, from about 14% w/w to about 19% w/w, from about 15% w/w to about 18% w/w, or from about 16% w/w to about 17% w/w of ethyl cellulose (or Eudragit S 100), based on the total weight of the composition. In certain embodiments, the functional coat comprises from about 1% w/w to about 4% w/w, from about 1.5% w/w to about 3.5% w/w, from about 2% w/w to about 3% w/w, from about 2.25% w/w to about 2.75% w/w, or about 2.5% w/w of hypromellose phthalate (or Hypromellose/Methocel E5 Prem LV), based on the total weight of the dosage form. In certain embodiments, the functional coat comprises from about 0.5% w/w to about 3% w/w, from about 1% w/w to about 2.5% w/w, from about 1.1% w/w to about 2.25% w/w, from about 1.2% w/w to about 2% w/w, from about 1.3% w/w to about 1.9% w/w, from about 1.4% w/w to about 1.8% w/w, from about 1.5% w/w to about 1.7% w/w, or about 1.6% w/w of triethyl citrate, based on the total weight of the dosage form. In certain embodiments, the functional coat comprises from about 1.5% w/w to about 5% w/w, from about 2% w/w to about 4.5% w/w, from about 2.5% w/w to about 4% w/w, from about 2.75% w/w to about 3.5% w/w, from about 3% w/w to about 3.4% w/w, from about 3.1% w/w to about 3.3% w/w, or about 3.3% w/w of talc, based on the total weight of the dosage form.

In certain embodiments, the pellets of the present disclosure comprise a core, a seal coat, a drug layer, and a functional coat. In certain embodiments, the present disclosure provides for pellets that comprise a core comprising tartaric acid; a seal coat comprising hypromellose, triethyl citrate, and talc; a drug layer comprising trihexyphenidyl hydrochloride, hypromellose, triethyl citrate and talc; a functional coat comprising ethyl cellulose, Eudragit S 100 (anionic copolymers based on methacrylic acid and methyl methacrylate), hypromellose phthalate, hypromellose, triethyl citrate and talc.

In certain embodiments, the pellets of the present disclosure comprise from about 10.00 mg to about 250.00 mg of tartaric acid in the core; from about 1.50 mg to about 8.50 mg of hypromellose, from about 0.05 mg to about 0.45 mg of triethyl citrate and from about 0.40 mg to about 2.00 mg of talc in the seal coat; from about 3.00 mg to about 7.00 mg of trihexyphenidyl hydrochloride, from about 1.00 mg to about 5.00 mg of hypromellose, from about 0.10 mg to about 0.20 mg of triethyl citrate, and from about 0.30 mg to about 1.00 mg of talc in the drug layer; optionally from about 5.00 mg to about 25.00 mg of ethyl cellulose, optionally from about 5.00 mg to about 15.00 mg of Eudragit S 100 (anionic copolymers based on methacrylic acid and methyl methacrylate), optionally from about 1.00 mg to about 7.00 mg of hypromellose phthalate, optionally from about 1.50 mg to about 2.50 mg of hypromellose, from about 0.50 mg to about 3.00 mg of triethyl citrate, and from about 1.00 to about 5.50 mg of talc in the functional coat. In certain embodiments, the pellets of the present disclosure comprise from about 50% w/w to about 75% w/w of tartaric acid in the core; from about 2.0% w/w to about 3.0% w/w of hypromellose, from about 0.10% w/w to about 0.20% w/w of triethyl citrate and from about 0.50% w/w to about 1.00% w/w of talc in the seal coat; from about 1.90% w/w to about 7.00% w/w of trihexyphenidyl hydrochloride, from about 1.00% w/w to about 5.00% w/w of hypromellose, from about 0.10% w/w to about 0.25% w/w of triethyl citrate, and from about 0.50% w/w to about 1.00% w/w of talc in the drug layer; optionally from about 8.00% w/w to about 15.00% w/w of ethyl cellulose, optionally from about 10.00% w/w to about 15.00% w/w of Eudragit S 100 (anionic copolymers based on methacrylic acid and methyl methacrylate), optionally from about 2.0% w/w to about 3.5% w/w of hypromellose phthalate, optionally from about 2.00% w/w to about 3.00% w/w of hypromellose, from about 1.00% w/w to about 2.00% w/w of triethyl citrate, and from about 2.00% w/w to about 4.00% w/w of talc in the functional coat, based on the total weight of the composition.

In a particular embodiment, a pellet of the present disclosure comprises about 70.98% w/w of tartaric acid in the core; about 2.73% w/w of hypromellose, about 0.14% w/w of triethyl citrate, and about 0.68% w/w talc in the seal coat; about 7.10% w/w of trihexyphenidyl hydrochloride, about 4.26% w/w of Hypromellose, about 0.21% w/w of triethyl citrate, and about 0.85% w/w of talc in the drug layer; about 8.04% w/w of ethyl cellulose, about 2.00% w/w of hypromellose phthalate, about 1.01% w/w of triethyl citrate, and about 2.00% w/w of talc in the functional coat, all amounts based on the total weight of the composition.

In another particular embodiment, a pellet of the present disclosure comprises about 79.50% w/w of tartaric acid in the core; about 3.06% w/w of hypromellose, about 0.15% w/w of triethyl citrate, and about 0.76% w/w talc in the seal coat; about 1.99% w/w of trihexyphenidyl hydrochloride, about 1.19% w/w of hypromellose, about 0.06% w/w of triethyl citrate, and about 0.24% w/w of talc in the drug layer; about 8.03% w/w of ethyl cellulose, about 2.01% w/w of hypromellose phthalate, about 1.00% w/w of triethyl citrate, and about 2.01% w/w of talc in the functional coat, all amounts based on the total weight of the composition.

In another particular embodiment, a pellet of the present disclosure comprises about 65.30% w/w of tartaric acid in the core; about 2.51% w/w of hypromellose, about 0.13% w/w of triethyl citrate, and about 0.63% w/w talc in the seal coat; about 6.53% w/w of trihexyphenidyl hydrochloride, about 3.92% w/w of hypromellose, about 0.20% w/w of triethyl citrate, and about 0.78% w/w of talc in the drug layer; about 13.07% w/w of ethyl cellulose, about 2.31% w/w of hypromellose phthalate, about 1.54% w/w of triethyl citrate, and about 3.08% w/w of talc in the functional coat, all amounts based on the total weight of the composition.

In another particular embodiment, a pellet of the present disclosure comprises about 60.47% w/w of tartaric acid in the core; about 2.51% w/w of hypromellose, about 0.13% w/w of triethyl citrate, and about 0.63% w/w talc in the seal coat; about 6.53% w/w of trihexyphenidyl hydrochloride, about 3.92% w/w of hypromellose, about 0.20% w/w of triethyl citrate, and about 0.78% w/w of talc in the drug layer; about 13.07% w/w of ethyl cellulose, about 2.31% w/w of hypromellose, about 1.54% w/w of triethyl citrate, and about 3.08% w/w of talc in the functional coat, all amounts based on the total weight of the composition.

In another particular embodiment, a pellet of the present disclosure comprises about 60.47% w/w of tartaric acid in the core; about 2.32% w/w of hypromellose, about 0.12% w/w of triethyl citrate, and about 0.58% w/w talc in the seal coat; about 6.05% w/w of trihexyphenidyl hydrochloride, about 3.63% w/w of hypromellose, about 0.18% w/w of triethyl citrate, and about 0.73% w/w of talc in the drug layer; about 16.95% w/w of ethyl cellulose, about 2.99% w/w of hypromellose phthalate, about 2.00% w/w of triethyl citrate, and about 3.99% w/w of talc in the functional coat, all amounts based on the total weight of the composition.

In another particular embodiment, a pellet of the present disclosure comprises about 65.31% w/w of tartaric acid in the core; about 2.51% w/w of hypromellose, about 0.13% w/w of triethyl citrate, and about 0.63% w/w talc in the seal coat; about 6.53% w/w of trihexyphenidyl hydrochloride, about 3.92% w/w of hypromellose, about 0.20% w/w of triethyl citrate, and about 0.78% w/w of talc in the drug layer; about 12.3% w/w of Eudragit S 100 (anionic copolymers based on methacrylic acid and methyl methacrylate), about 3.08% w/w of hypromellose phthalate, about 1.54% w/w of triethyl citrate, and about 3.07% w/w of talc in the functional coat, all amounts based on the total weight of the composition.

In another particular embodiment, a pellet of the present disclosure comprises about 68.03% w/w of tartaric acid in the core; about 2.61% w/w of hypromellose, about 0.14% w/w of triethyl citrate, and about 0.65% w/w talc in the seal coat; about 6.80% w/w of trihexyphenidyl hydrochloride, about 4.08% w/w of hypromellose, about 0.20% w/w of triethyl citrate, and about 0.82% w/w of talc in the drug layer; about 10.20% w/w of ethyl cellulose, about 2.56% w/w of hypromellose phthalate, about 1.29% w/w of triethyl citrate, and about 2.56% w/w of talc in the functional coat, all amounts based on the total weight of the composition.

In another particular embodiment, a pellet of the present disclosure comprises about 65.36% w/w of tartaric acid in the core; about 2.51% w/w of hypromellose, about 0.13% w/w of triethyl citrate, and about 0.63% w/w talc in the seal coat; about 6.54% w/w of trihexyphenidyl hydrochloride, about 3.92% w/w of hypromellose, about 0.20% w/w of triethyl citrate, and about 0.78% w/w of talc in the drug layer; about 13.0% w/w of ethyl cellulose, about 2.30% w/w of hypromellose phthalate, about 1.53% w/w of triethyl citrate, and about 3.07% w/w of talc in the functional coat, all amounts based on the total weight of the composition.

In certain embodiments, the pellets of the present disclosure comprise a core, a seal coat-1, a drug layer-1, a functional coat, a seal coat-2, a drug layer-2, and an over coat. In certain embodiments, the pellets of the present disclosure comprise from about 25.00% w/w to about 75.00% w/w or tartaric acid in the core; from about 1.50% w/w to about 3.00% w/w of hypromellose, from about 0.05% w/w to about 0.20% w/w of triethyl citrate, and from about 0.40% w/w to about 0.75% w/w of talc in the seal coat-1; from about 4.00% w/w to about 6.50% w/w of trihexyphenidyl hydrochloride, from about 2.50% w/w to about 4.00% w/w of hypromellose, from about 0.10% w/w to about 0.25% w/w of triethyl citrate, and from about 0.50% w/w to about 1.00% w/w of talc in the drug layer-1; from about 5.00% w/w to about 20.00% w/w of ethyl cellulose, from about 1.00 to about 3.50% w/w of hypromellose phthalate, from about 0.50% w/w to about 2.50% w/w of triethyl citrate, and from about 1.25% w/w to about 4.75% w/w of talc in the functional coat; optionally from about 2.75% w/w to about 4.50% w/w of hypromellose, optionally from about 0.70% w/w to about 1.10% w/w of talc, and optionally from about 0.05% w/w to about 0.25% w/w of triethyl citrate in the seal coat-2; optionally from about 0.50% w/w to about 1.50% w/w of trihexyphenidyl hydrochloride, optionally from about 0.50% w/w to about 1.00% w/w of succinic acid, optionally from about 1.00% w/w to about 2.50% w/w of tartaric acid, optionally from about 0.40% w/w to about 0.50% w/w of hypromellose, optionally from about 1.00% w/w to about 2.00% w/w of Copovidone, optionally from about 0.01% w/w to about 0.05% w/w talc, and optionally about 0.01% w/w of colloidal silicon dioxide in the drug layer-2; optionally from about 3.00% w/w to about 5.00% w/w of hypromellose, optionally from about 0.05% w/w to about 0.30% w/w of triethyl citrate, and from about 0.050% w/w to about 1.50% w/w of talc in the over coat, all amounts based on the total weight of the composition.

In a particular embodiment, a pellet of the present disclosure comprises about 58.65% w/w of tartaric acid in the core; about 2.25% w/w of hypromellose, about 0.12% w/w of triethyl citrate, about 0.56% w/w of talc in the seal coat-1; about 4.99% w/w of trihexyphenidyl hydrochloride, about 2.99% w/w of hypromellose, about 0.18% w/w of triethyl citrate, and about 0.65% w/w of talc in the drug layer-1; about 11.50% w/w of ethyl cellulose, about 2.05% w/w of hypromellose phthalate, about 1.35% w/w of triethyl citrate, and about 2.70% w/w of talc in the functional coat; about 3.45% w/w of hypromellose, about 0.88% w/w of talc, and about 0.09% w/w of triethyl citrate in the seal coat-2; about 0.88% w/w of trihexyphenidyl hydrochloride, about 0.88% w/w of succinic acid, about 0.53% w/w of hypromellose, about 0.02% w/w of triethyl citrate, about 0.53% w/w of talc, and about 0.01% w/w of colloidal silicon dioxide in the drug layer-2; about 3.73% w/w of hypromellose, about 0.08% w/w of triethyl citrate, and 0.94% w/w of talc in the over coat, all amounts based on the total weight of the composition.

In another particular embodiment, a pellet of the present disclosure comprises about 71.04% w/w of tartaric acid in the core; about 2.73% w/w of hypromellose, about 0.14% w/w of triethyl citrate, about 0.68% w/w of talc in the seal coat-1; about 7.10% w/w of trihexyphenidyl hydrochloride, about 4.26% w/w of hypromellose, about 0.21% w/w of triethyl citrate, and about 0.85% w/w of talc in the drug layer-1; about 8.50% w/w of ethyl cellulose, about 1.49% w/w of hypromellose phthalate, about 0.99% w/w of triethyl citrate, and about 1.99% w/w of talc in the functional coat, all amounts based on the total weight of the composition.

In another particular embodiment, a pellet of the present disclosure comprises about 63.79% w/w of tartaric acid in the core; about 2.45% w/w of hypromellose, about 0.13% w/w of triethyl citrate, about 0.61% w/w of talc in the seal coat-1; about 6.38% w/w of trihexyphenidyl hydrochloride, about 3.83% w/w of hypromellose, about 0.19% w/w of triethyl citrate, and about 0.77% w/w of talc in the drug layer-1; about 14.30% w/w of ethyl cellulose, about 2.51% w/w of hypromellose phthalate, about 1.68% w/w of triethyl citrate, and about 3.36% w/w of talc in the functional coat, all amounts based on the total weight of the composition.

In another particular embodiment, a pellet of the present disclosure comprises about 57.4% w/w of tartaric acid in the core; about 2.21% w/w of hypromellose, about 0.11% w/w of triethyl citrate, about 0.55% w/w of talc in the seal coat-1; about 5.75% w/w of trihexyphenidyl hydrochloride, about 3.45% w/w of hypromellose, about 0.17% w/w of triethyl citrate, and about 0.69% w/w of talc in the drug layer-1; about 19.34% w/w of ethyl cellulose, about 3.40% w/w of hypromellose phthalate, about 2.28% w/w of triethyl citrate, and about 4.55% w/w of talc in the functional coat, all amounts based on the total weight of the composition.

In another particular embodiment, a pellet of the present disclosure comprises about 54.79% w/w of tartaric acid in the core; about 2.10% w/w of hypromellose, about 0.11% w/w of triethyl citrate, about 0.53% w/w of talc in the seal coat-1; about 5.48% w/w of trihexyphenidyl hydrochloride, about 3.29% w/w of hypromellose, about 0.16% w/w of triethyl citrate, and about 0.66% w/w of talc in the drug layer-1; about 21.50% w/w of ethyl cellulose, about 3.78% w/w of hypromellose phthalate, about 2.53% w/w of triethyl citrate, and about 5.06% w/w of talc in the functional coat, all amounts based on the total weight of the composition.

In another particular embodiment, a pellet of the present disclosure comprises about 57.30% w/w of tartaric acid in the core; about 2.20% w/w of hypromellose, about 0.11% w/w of triethyl citrate, about 0.55% w/w of talc in the seal coat-1; about 4.87% w/w of trihexyphenidyl hydrochloride, about 2.92% w/w of hypromellose, about 0.17% w/w of triethyl citrate, and about 0.63% w/w of talc in the drug layer-1; about 11.20% w/w of ethyl cellulose, about 2.01% w/w of hypromellose phthalate, about 1.32% w/w of triethyl citrate, and about 2.64% w/w of talc in the functional coat; about 3.30% w/w of hypromellose, about 0.83% w/w of talc, and about 0.17% w/w of triethyl citrate in the seal coat-2; about 0.86% w/w of trihexyphenidyl hydrochloride, about 1.72% w/w of tartaric acid, about 1.24% w/w of Copovidone, and about 1.15% w/w of talc, in the drug layer-2; about 3.61% w/w of hypromellose, about 0.18% w/w of triethyl citrate, and about 0.91% w/w of talc in the over coat, all amounts based on the total weight of the composition.

In another particular embodiment, a pellet of the present disclosure comprises about 52.85% w/w of tartaric acid in the core; about 2.43% w/w of hypromellose, about 0.13% w/w of triethyl citrate, about 0.60% w/w of talc in the seal coat-1; about 5.39% w/w of trihexyphenidyl hydrochloride, about 3.23% w/w of hypromellose, about 0.19% w/w of triethyl citrate, and about 0.70% w/w of talc in the drug layer-1; about 12.43% w/w of ethyl cellulose, about 2.22% w/w of hypromellose phthalate, about 1.46% w/w of triethyl citrate, and about 2.92% w/w of talc in the functional coat; about 3.65% w/w of hypromellose, about 0.91% w/w of talc, and about 0.19% w/w of triethyl citrate in the seal coat-2; about 0.95% w/w of trihexyphenidyl hydrochloride, about 1.90% w/w of tartaric acid, about 1.37% w/w of Copovidone, and about 1.27% w/w of talc, in the drug layer-2; about 4.00% w/w of hypromellose, about 0.20% w/w of triethyl citrate, and about 1.00% w/w of talc in the over coat, all amounts based on the total weight of the composition. In another particular embodiment, a pellet of the present disclosure comprises about 47.29% w/w of tartaric acid in the core; about 2.72% w/w of hypromellose, about 0.14% w/w of triethyl citrate, about 0.68% w/w of talc in the seal coat-1; about 6.03% w/w of trihexyphenidyl hydrochloride, about 3.59% w/w of hypromellose, about 0.21% w/w of triethyl citrate, and about 0.78% w/w of talc in the drug layer-1; about 13.90% w/w of ethyl cellulose, about 2.46% w/w of hypromellose phthalate, about 1.63% w/w of triethyl citrate, and about 3.26% w/w of talc in the functional coat; about 4.09% w/w of hypromellose, about 1.02% w/w of talc, and about 0.21% w/w of triethyl citrate in the seal coat-2; about 1.06% w/w of trihexyphenidyl hydrochloride, about 2.13% w/w of tartaric acid, about 1.53% w/w of Copovidone, and about 1.42% w/w of talc, in the drug layer-2; about 4.46% w/w of hypromellose, about 0.23% w/w of triethyl citrate, and about 1.14% w/w of talc in the over coat, all amounts based on the total weight of the composition.

In another particular embodiment, a pellet of the present disclosure comprises about 58.53% w/w of tartaric acid in the core; about 2.25% w/w of hypromellose, about 0.12% w/w of triethyl citrate, about 0.56% w/w of talc in the seal coat-1; about 5.41% w/w of trihexyphenidyl hydrochloride, about 3.25% w/w of hypromellose, about 0.19% w/w of triethyl citrate, and about 0.70% w/w of talc in the drug layer-1; about 11.60% w/w of ethyl cellulose, about 2.07% w/w of hypromellose phthalate, about 1.36% w/w of triethyl citrate, and about 2.72% w/w of talc in the functional coat; about 3.46% w/w of hypromellose, about 0.88% w/w of talc, and about 0.09% w/w of triethyl citrate in the seal coat-2; about 0.44% w/w of trihexyphenidyl hydrochloride, about 0.44% w/w of succinic acid, about 0.14% w/w of hypromellose, about 0.02% w/w of triethyl citrate, about 0.53% w/w of talc, and about 0.01% w/w of colloidal silicon dioxide in the drug layer-2; about 3.73% w/w of hypromellose, about 0.08% w/w of triethyl citrate, and about 0.94% w/w of talc in the over coat, all amounts based on the total weight of the composition.

In another particular embodiment, a pellet of the present disclosure comprises about 10.00 mg of tartaric acid in the core; about 0.384 mg of hypromellose, about 0.02 mg of triethyl citrate, about 0.096 mg of talc in the seal coat-1; about 0.925 mg of trihexyphenidyl hydrochloride, about 0.555 mg of hypromellose, about 0.333 mg of triethyl citrate, and about 0.120 mg of talc in the drug layer-1; about 1.982 mg of ethyl cellulose, about 0.354 mg of hypromellose phthalate, about 0.233 mg of triethyl citrate, and about 0.465 mg of talc in the functional coat; about 0.591 mg of hypromellose, about 0.151 mg of talc, and about 0.016 mg of triethyl citrate in the seal coat-2; about 0.075 mg of trihexyphenidyl hydrochloride, about 0.075 mg of succinic acid, about 0.023 mg of hypromellose, about 0.004 mg of triethyl citrate, about 0.90 mg of talc, and about 0.002 mg of colloidal silicon dioxide in the drug layer-2; about 0.636 mg of hypromellose, about 0.014 mg of triethyl citrate, and about 0.160 mg of talc in the over coat.

In another particular embodiment, a pellet of the present disclosure comprises about 20.00 mg of tartaric acid in the core; about 0.77 mg of hypromellose, about 0.04 mg of triethyl citrate, about 0.192 mg of talc in the seal coat-1; about 1.850 mg of trihexyphenidyl hydrochloride, about 1.110 mg of hypromellose, about 0.065 mg of triethyl citrate, and about 0.239 mg of talc in the drug layer-1; about 3.963 mg of ethyl cellulose, about 0.708 mg of hypromellose phthalate, about 0.465 mg of triethyl citrate, and about 0.930 mg of talc in the functional coat; about 1.183 mg of hypromellose, about 0.302 mg of talc, and about 0.032 mg of triethyl citrate in the seal coat-2; about 0.15 mg of trihexyphenidyl hydrochloride, about 0.15 mg of succinic acid, about 0.05 mg of hypromellose, about 0.01 mg of triethyl citrate, and about 0.18 mg of talc in the drug layer-2; about 1.27 mg of hypromellose, about 0.03 mg of triethyl citrate, and about 0.32 mg of talc in the over coat.

In another particular embodiment, a pellet of the present disclosure comprises about 60.00 mg of tartaric acid in the core; about 2.304 mg of hypromellose, about 0.120 mg of triethyl citrate, about 0.576 mg of talc in the seal coat-1; about 5.550 mg of trihexyphenidyl hydrochloride, about 3.330 mg of hypromellose, about 0.196 mg of triethyl citrate, and about 0.718 mg of talc in the drug layer-1; about 11.890 mg of ethyl cellulose, about 2.123 mg of hypromellose phthalate, about 1.395 mg of triethyl citrate, and about 2.790 mg of talc in the functional coat; about 3.548 mg of hypromellose, about 0.905 mg of talc, and about 0.097 mg of triethyl citrate in the seal coat-2; about 0.45 mg of trihexyphenidyl hydrochloride, about 0.45 mg of succinic acid, about 0.14 mg of hypromellose, about 0.02 mg of triethyl citrate, about 0.54 mg of talc, and about 0.01 mg of colloidal silicon dioxide in the drug layer-2; about 3.82 mg of hypromellose, about 0.08 mg of triethyl citrate, and about 0.96 mg of talc in the over coat.

In another particular embodiment, a pellet of the present disclosure comprises about 80.00 mg of tartaric acid in the core; about 3.072 mg of hypromellose, about 0.16 mg of triethyl citrate, about 0.768 mg of talc in the seal coat-1; about 7.400 mg of trihexyphenidyl hydrochloride, about 4.440 mg of hypromellose, about 0.261 mg of triethyl citrate, and about 0.958 mg of talc in the drug layer-1; about 15.853 mg of ethyl cellulose, about 2.831 mg of hypromellose phthalate, about 1.860 mg of triethyl citrate, and about 3.721 mg of talc in the functional coat; about 4.731 mg of hypromellose, about 1.207 mg of talc, and about 0.129 mg of triethyl citrate in the seal coat-2; about 0.60 mg of trihexyphenidyl hydrochloride, about 0.60 mg of succinic acid, about 0.18 mg of hypromellose, about 0.03 mg of triethyl citrate, about 0.72 mg of talc, and about 0.02 mg of colloidal silicon dioxide in the drug layer-2; about 5.09 mg of hypromellose, about 0.11 mg of triethyl citrate, and about 1.28 mg of talc in the over coat.

In another particular embodiment, a pellet of the present disclosure comprises about 100.00 mg of tartaric acid in the core; about 3.84 mg of hypromellose, about 0.20 mg of triethyl citrate, about 0.96 mg of talc in the seal coat-1; about 9.250 mg of trihexyphenidyl hydrochloride, about 5.550 mg of hypromellose, about 0.326 mg of triethyl citrate, and about 1.197 mg of talc in the drug layer-1; about 19.816 mg of ethyl cellulose, about 3.539 mg of hypromellose phthalate, about 2.325 mg of triethyl citrate, and about 4.651 mg of talc in the functional coat; about 5.913 mg of hypromellose, about 1.508 mg of talc, and about 0.161 mg of triethyl citrate in the seal coat-2; about 0.75 mg of trihexyphenidyl hydrochloride, about 0.75 mg of succinic acid, about 0.23 mg of hypromellose, about 0.04 mg of triethyl citrate, about 0.90 mg of talc, and about 0.02 mg of colloidal silicon dioxide in the drug layer-2; about 6.36 mg of hypromellose, about 0.14 mg of triethyl citrate, and about 1.60 mg of talc in the over coat.

6.3. Compositions

In certain embodiments, the present disclosure provides compositions comprising capsules containing a final blend comprising extended release trihexyphenidyl hydrochloride pellets, colloidal silicon dioxide, and talc.

In certain embodiments, the final blend comprises from about 30 mg to about 200 mg, from about 35 mg to about 175 mg, from about 40 mg to about 150 mg, from about 45 mg to about 125 mg, or from about 50 mg to about 100 mg of extended release THP pellets. In certain embodiments, the final blend comprises from about 0.01 mg to about 0.5 mg, from about 0.05 mg to about 0.4 mg, from about 0.1 mg to about 0.3 mg, or from about 0.2 mg to about 0.25 mg of colloidal silicon dioxide. In certain embodiments, the final blend comprises from about 0.05 mg to about 0.6 mg, from about 0.1 mg to about 0.5 mg, from about 0.15 mg to about 0.4 mg, from about 0.2 mg to about 0.3 mg, or about 0.25 mg of talc.

In certain embodiments, the final blend comprises from about 30 mg to about 200 mg, from about 35 mg to about 175 mg, from about 40 mg to about 150 mg, from about 45 mg to about 125 mg, or from about 50 mg to about 100 mg of extended release THP pellets; from about 0.01 mg to about 0.5 mg, from about 0.05 mg to about 0.4 mg, from about 0.1 mg to about 0.3 mg, or from about 0.2 mg to about 0.25 mg of colloidal silicon dioxide; and from about 0.05 mg to about 0.6 mg, from about 0.1 mg to about 0.5 mg, from about 0.15 mg to about 0.4 mg, from about 0.2 mg to about 0.3 mg, or about 0.25 mg of talc. In certain embodiments, the final blend comprises from about 97% w/w to about 99.7%/w/w of extended release THP pellets; from about 0.2% w/w to about 0.3% w/w of colloidal silicon dioxide; and from about 0.2% w/w to about 0.3% w/w of talc.

In a particular embodiment, the final blend of the present disclosure comprises about 102.01 mg of THP pellets, about 0.25 mg of colloidal silicon dioxide, and about 0.25 mg of talc. In another particular embodiment, the final blend of the present disclosure comprises about 17.002 mg of THP pellets, about 0.042 mg of colloidal silicon dioxide, and about 0.042 mg of talc. In another particular embodiment, the final blend of the present disclosure comprises about 34.004 mg of THP pellets, about 0.08 mg of colloidal silicon dioxide, and about 0.08 mg of talc. In another particular embodiment, the final blend of the present disclosure comprises about 102.013 mg of THP pellets, about 0.25 mg of colloidal silicon dioxide, and about 0.25 mg of talc. In another particular embodiment, the final blend of the present disclosure comprises about 136.018 mg of THP pellets, about 0.33 mg of colloidal silicon dioxide, and about 0.33 mg of talc. In another particular embodiment, the final blend of the present disclosure comprises about 170.022 mg of THP pellets, about 0.42 mg of colloidal silicon dioxide, and about 0.42 mg of talc.

6.4. Methods of Making

In certain embodiments, the present disclosure provides extended release trihexyphenidyl compositions maintaining therapeutically effective stable plasma concentrations of THP or a pharmaceutically acceptable salt thereof, without burst release/dose dumping. In certain embodiments, the compositions of the disclosure provide extended release of THP or a pharmaceutically acceptable salt thereof for at least about 12 hours, e.g., about 16 hours.

The extended release trihexyphenidyl compositions of the disclosure include extended release pellets suitable for dosing in capsules, sachets, and as sprinkles on food. In certain embodiments, the extended release pellets comprise a core comprising an organic acid; a seal coat comprising a water-soluble, nonionic polymer over the core comprising organic acid; a drug layer comprising trihexyphenidyl hydrochloride over the seal coat; and a functional coat/rate controlling membrane, comprising a water-insoluble polymer, an enteric polymer, and a plasticizer, over the drug layer. In certain embodiments, the presence of seal coat is optional. In certain embodiments, the core is a nonpareil seed coated with an organic acid. In certain embodiments, the organic acid coat over the nonpareil seed contains trihexyphenidyl. In certain embodiments, the core comprising organic acid is coated with a coat containing trihexyphenidyl hydrochloride and additional organic acid. In certain embodiments, the additional organic acid in the coating can be the same as the organic acid present in the core. In certain embodiments, the additional organic acid in the coating can be different from the organic acid present in the core. In certain embodiments, the extended release pellets are made by coating the core comprising an organic acid with a seal coat, coating the seal-coated core with a drug layer comprising trihexyphenidyl hydrochloride, and coating the drug-layered pellet with a functional coat/membrane comprising ethyl cellulose and HP 55 (hypromellose phthalate). In certain embodiments, the functional coat is further coated with an immediate release drug layer containing trihexyphenidyl hydrochloride for immediate release. In certain embodiments, there is a seal coat between the functional coat and drug layer-2. In certain embodiments, the presence of the seal coat and/or drug layer-2 is optional. In certain embodiments, the immediate release drug layer contains trihexyphenidyl hydrochloride and an organic acid. In certain embodiments, the organic acid in the core and the immediate release drug layer are different.

6.5. Methods of Use

In certain embodiments, the disclosure provides methods for treating symptoms of Parkinson's disease, cerebral palsy, dystonia, sialorrhea, dyskinesia, dystonia associated with cerebral palsy, and any other disease or disorder for which trihexyphenidyl is an appropriate treatment. The methods comprise administering to the patient an extended release trihexyphenidyl composition of the disclosure suitable for once- or twice-daily administration.

In certain embodiments, the disclosure provides a method for improving patient compliance by administering the extended release trihexyphenidyl compositions of the disclosure, wherein the composition provides a reduced $C_{max}$, and increased trough-to-peak concentration ratios ($C_{min}:C_{max}$) of ≥0.4, as compared to marketed trihexyphenidyl tablets. FIG. 8 compares pharmacokinetic data for Artane IR (5 mg BID), and Artane ER (10 mg QD) (see, Cheung et al. (1988), supra) with a 5 mg extended release composition of the disclosure (Test T) (normalized to 10 mg). FIG. 8 demonstrates that Pellet 9 exhibits reduced variability (e.g., increased $C_{min}:C_{max}$ ratio) in the plasma concentration of THP over an extended time period compared to Artane ER (10 mg) and Artane IR (5 mg BID).

In certain embodiments, the disclosure provides methods for reducing side effects associated with currently marketed immediate release trihexyphenidyl compositions. In certain embodiments, the methods comprise administering extended release trihexyphenidyl compositions of the disclosure that (1) reduce initial burst release/dose dumping and (2) maintain therapeutic plasma concentrations of the drug for extended periods of time. In certain embodiments, the therapeutic plasma concentrations depend on the severity of the patient's condition, and on the strength of the THP composition administered to the patient. In certain embodiments, the compositions of the disclosure contain between about 5% and about 10% w/w, based on the total weight of the composition, of THP HCl.

In certain embodiments, the disclosure provides methods for improving patient compliance by administering extended release trihexyphenidyl compositions of the disclosure, wherein the extended release compositions will allow for reduced frequency of administration of the composition, improve patient compliance, and reduce side effects associated with high $C_{max}$ levels and low $C_{min}:C_{max}$ ratios (i.e., <0.4). In certain embodiments, the compositions of the disclosure avoid initial burst release ($C_{max}$ above the therapeutic range) while providing therapeutically effective amounts of trihexyphenidyl hydrochloride for periods of about 12 hours to about 24 hours.

In certain embodiments, the disclosure provides methods for improving patient compliance by administering extended release trihexyphenidyl compositions that avoid an initial burst release of trihexyphenidyl hydrochloride, suitable for once- or twice-daily administration, and provide desired therapeutic effects with minimal side effects, such as drowsiness, dizziness or blurred vision, dry mouth, stomach upset, vomiting, diarrhea, constipation, and difficulty in urinating, which side effects are associated with high peak serum concentrations ($C_{max}$) and low trough-to-peak concentration ratios ($C_{min}:C_{max}$). The methods comprise administering to the patient extended release trihexyphenidyl compositions of the disclosure.

The following Examples illustrate the disclosure in a nonlimiting manner. Unless indicated to the contrary, the numerical parameters set forth herein can vary depending upon the desired properties sought to be obtained by the present disclosure.

7. EXAMPLES

Example 1: Preparation of Extended Release Trihexyphenidyl Hydrochloride Pellets (5 Mg)

The present Example provides a summary of the preparation of twenty-two pellets as shown in Tables 1, 2, and 3. Pellets 18-22 in Table 3 are dose proportional to Pellet 17.

TABLE 1

| Composition | Pellet 1 % w/w | Pellet 2 % w/w | Pellet 3 % w/w | Pellet 4 % w/w | Pellet 5 % w/w | Pellet 6 % w/w | Pellet 7 % w/w | Pellet 8 % w/w |
|---|---|---|---|---|---|---|---|---|
| Core | | | | | | | | |
| Tartaric acid | 70.98 | 79.50 | 65.30 | 65.30 | 60.47 | 65.31 | 68.03 | 65.36 |
| Seal Coat | | | | | | | | |
| Hypromellose (Methocel E5 Premium LV) | 2.73 | 3.06 | 2.51 | 2.51 | 2.32 | 2.51 | 2.61 | 2.51 |
| Triethyl citrate | 0.14 | 0.15 | 0.13 | 0.13 | 0.12 | 0.13 | 0.14 | 0.13 |
| Talc | 0.68 | 0.76 | 0.63 | 0.63 | 0.58 | 0.63 | 0.65 | 0.63 |
| Coating Solvent* | Ethanol:Water (70:30) q.s. | | | | | | | |
| Drug Layer | | | | | | | | |
| Trihexyphenidyl hydrochloride | 7.10 | 1.99 | 6.53 | 6.53 | 6.05 | 6.53 | 6.80 | 6.54 |
| Hypromellose (Methocel E5 Premium LV) | 4.26 | 1.19 | 3.92 | 3.92 | 3.63 | 3.92 | 4.08 | 3.92 |
| Triethyl citrate | 0.21 | 0.06 | 0.20 | 0.20 | 0.18 | 0.20 | 0.20 | 0.20 |
| Talc | 0.85 | 0.24 | 0.78 | 0.78 | 0.73 | 0.78 | 0.82 | 0.78 |
| Coating Solvent* | Ethanol:Water (80:20) q.s. | | | | | | | |
| Functional Coat | | | | | | | | |
| Ethyl cellulose 20 cps | 8.04 | 8.03 | 13.07 | 13.07 | 16.95 | NA | 10.26 | 13.03 |
| Eudragit S 100 | NA | NA | NA | NA | NA | 12.30 | NA | NA |
| Hypromellose phthalate (HP 55) | 2.00 | 2.01 | 2.31 | NA | 2.99 | 3.08 | 2.56 | 2.30 |
| Hypromellose (Methocel E5 Premium LV) | NA | NA | NA | 2.31 | NA | NA | NA | NA |
| Triethyl citrate | 1.01 | 1.00 | 1.54 | 1.54 | 2.00 | 1.54 | 1.29 | 1.53 |
| Talc | 2.00 | 2.01 | 3.08 | 3.08 | 3.99 | 3.07 | 2.56 | 3.07 |
| Coating Solvent* | Ethanol:Water (70:30) q.s. | | | | | | | |
| Total Weight | 100.00 | 100.00 | 100.00 | 100.00 | 100.00 | 100.00 | 100.00 | 100.00 |

*Removed during process

TABLE 2

| Composition | Pellet 9 % w/w | Pellet 10 % w/w | Pellet 11 % w/w | Pellet 12 % w/w | Pellet 13 % w/w | Pellet 14 % w/w | Pellet 15 % w/w | Pellet 16 % w/w |
|---|---|---|---|---|---|---|---|---|
| Core | | | | | | | | |
| Tartaric acid | 58.65 | 71.04 | 63.79 | 57.49 | 54.79 | 57.35 | 52.85 | 47.29 |
| Seal Coat-1 | | | | | | | | |
| Hypromellose (Methocel E5 Premium LV) | 2.25 | 2.73 | 2.45 | 2.21 | 2.10 | 2.20 | 2.43 | 2.72 |
| Triethyl citrate | 0.12 | 0.14 | 0.13 | 0.11 | 0.11 | 0.11 | 0.13 | 0.14 |
| Talc | 0.56 | 0.68 | 0.61 | 0.55 | 0.53 | 0.55 | 0.60 | 0.68 |

TABLE 2-continued

| Composition | Pellet 9 % w/w | Pellet 10 % w/w | Pellet 11 % w/w | Pellet 12 % w/w | Pellet 13 % w/w | Pellet 14 % w/w | Pellet 15 % w/w | Pellet 16 % w/w |
|---|---|---|---|---|---|---|---|---|
| Coating Solvent* | Ethanol:Water (70:30) q s. | | | | | | | |
| Drug Layer-1 | | | | | | | | |
| Trihexyphenidyl hydrochloride | 4.99 | 7.10 | 6.38 | 5.75 | 5.48 | 4.87 | 5.39 | 6.03 |
| Hypromellose (Methocel E5 Premium LV) | 2.99 | 4.26 | 3.83 | 3.45 | 3.29 | 2.92 | 3.23 | 3.59 |
| Triethyl citrate | 0.18 | 0.21 | 0.19 | 0.17 | 0.16 | 0.17 | 0.19 | 0.21 |
| Talc | 0.65 | 0.85 | 0.77 | 0.69 | 0.66 | 0.63 | 0.70 | 0.78 |
| Coating Solvent* | Ethanol:Water (80:20) q s. | | | | | | | |
| Functional Coat | | | | | | | | |
| Ethyl cellulose 20 cps | 11.50 | 8.50 | 14.30 | 19.34 | 21.50 | 11.24 | 12.43 | 13.90 |
| Hypromellose phthalate (HP 55) | 2.05 | 1.49 | 2.51 | 3.40 | 3.78 | 2.01 | 2.22 | 2.46 |
| Triethyl citrate | 1.35 | 0.99 | 1.68 | 2.28 | 2.53 | 1.32 | 1.46 | 1.63 |
| Talc | 2.70 | 1.99 | 3.36 | 4.55 | 5.06 | 2.64 | 2.92 | 3.26 |
| Coating Solvent* | Ethanol:Water (70:30) q s. | | | | | | | |
| Seal Coat-2 | | | | | | | | |
| Hypromellose (Methocel E5 Premium LV) | 3.45 | NA | NA | NA | NA | 3.30 | 3.65 | 4.09 |
| Talc | 0.88 | NA | NA | NA | NA | 0.83 | 0.91 | 1.02 |
| Triethyl citrate | 0.09 | NA | NA | NA | NA | 0.17 | 0.19 | 0.21 |
| Coating Solvent* | Ethanol:Water (70:30) q s. | | | | | | | |
| Drug Layer-2 | | | | | | | | |
| Trihexyphenidyl hydrochloride | 0.88 | NA | NA | NA | NA | 0.86 | 0.95 | 1.06 |
| Succinic acid | 0.88 | NA | NA | NA | NA | NA | NA | NA |
| Tartaric acid | NA | NA | NA | NA | NA | 1.72 | 1.90 | 2.13 |
| Hypromellose (Methocel E5 Premium LV) | 0.53 | NA | NA | NA | NA | NA | NA | NA |
| Copovidone | NA | NA | NA | NA | NA | 1.24 | 1.37 | 1.53 |
| Triethyl citrate | 0.02 | NA | NA | NA | NA | NA | NA | NA |
| Talc | 0.53 | NA | NA | NA | NA | 1.15 | 1.27 | 1.42 |
| Colloidal silicon dioxide | 0.01 | NA | NA | NA | NA | NA | NA | NA |
| Coating Solvent* | Ethanol:Water (80:20) q s. | | | | | | | |
| Over Coat | | | | | | | | |
| Hypromellose (Methocel E5 Premium LV) | 3.73 | NA | NA | NA | NA | 3.61 | 4.00 | 4.46 |
| Triethyl citrate | 0.08 | NA | NA | NA | NA | 0.18 | 0.20 | 0.23 |
| Talc | 0.94 | NA | NA | NA | NA | 0.91 | 1.00 | 1.14 |
| Coating Solvent* | Ethanol:Water (70:30) q s. | | | | | | | |
| Total Weight | 100.00 | 100.00 | 100.00 | 100.00 | 100.00 | 100.00 | 100.00 | 100.00 |

*Removed during process

TABLE 3

| Composition | Pellet 17 % w/w(mg) | Pellet 18 (mg) | Pellet 19 (mg) | Pellet 20 (mg) | Pellet 21 (mg) | Pellet 22 (mg) |
|---|---|---|---|---|---|---|
| Core | | | | | | |
| Tartaric acid | 58.53 (50) | 10.0 | 20.0 | 60.0 | 80.0 | 100.0 |
| Seal Coat-1 | | | | | | |
| Hypromellose (Methocel E5 Premium LV) | 2.25 (1.92) | 0.384 | 0.77 | 2.304 | 3.072 | 3.84 |
| Triethyl citrate | 0.12 (0.10) | 0.02 | 0.04 | 0.120 | 0.16 | 0.2 |
| Talc | 0.56 (0.48) | 0.096 | 0.192 | 0.576 | 0.768 | 0.96 |
| Coating Solvent* | Ethanol:Water (70:30) q.s. | | | | | |
| Drug Layer-1 | | | | | | |
| Trihexyphenidyl hydrochloride | 5.41 (4.625) | 0.925 | 1.850 | 5.550 | 7.400 | 9.250 |
| Hypromellose (Methocel E5 Premium LV) | 3.25 (2.775) | 0.555 | 1.110 | 3.330 | 4.440 | 5.550 |
| Triethyl citrate | 0.19 (0.163) | 0.333 | 0.065 | 0.196 | 0.261 | 0.326 |
| Talc | 0.70 (0.599) | 0.120 | 0.239 | 0.718 | 0.958 | 1.197 |
| Coating Solvent* | Ethanol:Water (80:20) q.s. | | | | | |
| Functional Coat | | | | | | |
| Ethyl cellulose 20 cps | 11.60 (9.91) | 1.982 | 3.963 | 11.890 | 15.853 | 19.816 |
| Hypromellose phthalate (HP 55) | 2.07 (1.77) | 0.354 | 0.708 | 2.123 | 2.831 | 3.539 |
| Triethyl citrate | 1.36 (1.16) | 0.233 | 0.465 | 1.395 | 1.860 | 2.325 |
| Talc | 2.72 (2.33) | 0.465 | 0.930 | 2.790 | 3.721 | 4.651 |
| Coating Solvent* | Ethanol:Water (70:30) q.s. | | | | | |
| Seal Coat-2 | | | | | | |
| Hypromellose (Methocel E5 Premium LV) | 3.46 (2.96) | 0.591 | 1.183 | 3.548 | 4.731 | 5.913 |
| Talc | 0.88 (0.75) | 0.151 | 0.302 | 0.905 | 1.207 | 1.508 |
| Triethyl citrate | 0.09 (0.08) | 0.016 | 0.032 | 0.097 | 0.129 | 0.161 |
| Coating Solvent* | Ethanol:Water (70:30) q.s. | | | | | |
| Drug layer-2 | | | | | | |
| Trihexyphenidyl hydrochloride | 0.44 (0.375) | 0.075 | 0.15 | 0.45 | 0.60 | 0.75 |
| Succinic acid | 0.44 (0.375) | 0.075 | 0.15 | 0.45 | 0.60 | 0.75 |
| Hypromellose (Methocel E5 Premium LV) | 0.14 (0.113) | 0.023 | 0.05 | 0.14 | 0.18 | 0.23 |
| Triethyl citrate | 0.02 (0.02) | 0.004 | 0.01 | 0.02 | 0.03 | 0.04 |
| Talc | 0.53 (0.450) | 0.090 | 0.18 | 0.54 | 0.72 | 0.90 |
| Colloidal silicon dioxide | 0.01 (0.010) | 0.002 | 0.00 | 0.01 | 0.02 | 0.02 |
| Coating Solvent* | Ethanol:Water (80:20) q.s. | | | | | |
| Over Coat (5% of IR layered pellets) | | | | | | |
| Hypromellose (Methocel E5 Premium LV) | 3.73 (3.18) | 0.636 | 1.27 | 3.82 | 5.09 | 6.36 |
| Triethyl citrate | 0.08 (0.07) | 0.014 | 0.03 | 0.08 | 0.11 | 0.14 |
| Talc | 0.94 (0.80) | 0.160 | 0.32 | 0.96 | 1.28 | 1.60 |
| Total weight | 99.52 (85.01) | 17.004 | 34.009 | 102.012 | 135.969 | 170.026 |
| Coating Solvent* | Ethanol:Water (70:30) q.s. | | | | | |
| Final Blend | | | | | | |
| THP over coated pellets | 99.52 (102.01) | 17.002 | 34.004 | 102.013 | 136.018 | 170.022 |
| Colloidal silicon dioxide | 0.24 (0.25) | 0.042 | 0.08 | 0.25 | 0.33 | 0.42 |

TABLE 3-continued

| Composition | Pellet 17 % w/w(mg) | Pellet 18 (mg) | Pellet 19 (mg) | Pellet 20 (mg) | Pellet 21 (mg) | Pellet 22 (mg) |
|---|---|---|---|---|---|---|
| Talc | 0.24 (0.25) | 0.042 | 0.08 | 0.25 | 0.33 | 0.42 |
| Total fill weight in capsule | 100.00 (102.51) | 17.086 | 34.171 | 102.513 | 136.684 | 170.855 |

*Removed during process

Manufacturing Procedure:
A. Seal Coat-1:
A-1: Hypromellose was added to a mixture of ethanol (200 proof) and water (70:30 w/w ratio) in a stainless steel container and mixed until a clear solution was obtained.
A-2: To the clear solution from step #A-1, triethyl citrate was added and mixed for not less than 15 minutes to obtain a clear solution.
A-3: To the clear solution from step #A-2, talc was added and mixed until a uniform dispersion was obtained.
A-4: Cores comprising tartaric acid were taken in a Wurster chamber and seal coated with the dispersion from step #A-3 until target coating weight gain was achieved.
B. Drug Layer-1:
B-1: Trihexyphenidyl hydrochloride was added to a mixture of ethanol (200 proof) and water (80:20 w/w ratio) in a stainless steel container and mixed until a clear solution was obtained.
B-2: To the clear solution from step #B-1, hypromellose was added with constant stirring and mixed until a clear solution was obtained.
B-3: To the clear solution from step #B-2, triethyl citrate was added and mixed for not less than 15 minutes to obtain a clear solution.
B-4: To the clear solution from step #B-3, talc was added and mixed until a uniform dispersion was obtained.
B-5: Seal coated pellets from procedure A were taken in a Wurster chamber and coated with the dispersion from step #B-4.
C. Functional Coat:
C-1: Ethyl cellulose 20 cps or Eudragit S100 was added to ethanol (200 proof) in a stainless steel container and mixed until a clear solution was obtained.
C-2: To the clear solution from step #C-1, water was added and mixed for not less than 30 minutes to obtain a clear solution.
C-3: To the clear solution from step #C-2, hypromellose phthalate or hypromellose was added and mixed until a clear or light hazy solution was obtained.
C-4: To the solution from step #C-3, triethyl citrate was added and mixed for not less than 15 minutes to obtain a clear solution.
C-5: To the clear solution from step #C-4, talc was added and mixed to obtain a uniform dispersion.
C-6: Drug layered pellets from procedure B were taken in a Wurster chamber and coated with the dispersion from step #C-5 until target coating weight gain was achieved.
C-7: Functional coated pellets from step #C-6 were cured at about 25° C. for about 2 hours.
D. Seal Coat-2:
D-1: Hypromellose was added to a mixture of ethanol 200 proof and water (70:30 w/w ratio) in a stainless steel container and mixed until a clear solution was obtained.
D-2: To the solution from step #D-1, triethyl citrate was added and mixed for not less than 15 minutes to obtain a clear solution.
D-3: To the solution from step #D-2, talc was added and mixed until a uniform dispersion was obtained.
D-4: Functional coated pellets (pellets 9, and 14-22) from Step C were taken in a Wurster chamber and seal coated with the dispersion from step #D-3 until target coating weight gain was achieved.
E. Drug Layer-2:
E-1: Trihexyphenidyl hydrochloride and succinic acid were added to a mixture of ethanol (200 proof) and water (80:20 w/w ratio) in a stainless steel container and mixed to form a clear solution.
E-2: To the solution from step #E-1, hypromellose was added with constant stirring and mixed until a clear solution was obtained.
E-3: To the solution from step #E-2, triethyl citrate was added and mixed for not less than 15 minutes to obtain a clear solution.
E-4: To the clear solution from step #E-3, colloidal silicon dioxide and talc were added and mixed until a uniform dispersion was obtained.
E-5: Pellets with seal coat-2 (Pellets 9 and 14-22) from Step D were taken in a Wurster chamber and coated with the dispersion from step #E-4.
F. Over Coat:
F-1: Hypromellose was added to a mixture of ethanol 200 proof and water (70:30 w/w ratio) in a stainless steel container and mixed until a clear solution was obtained.
F-2: To the solution from step #F-1, triethyl citrate was added and mixed for not less than 15 minutes to obtain a clear solution.
F-3: To the clear solution from step #F-2, talc was added and mixed until a uniform dispersion was obtained.
F-4: Pellets with drug layer-2 (Pellets 9 and 14-22) from Step E were taken in a Wurster chamber and coated with the dispersion from step #F-3 until target coating weight gain was achieved.
G. Trihexyphenidyl Hydrochloride Capsules:
G-1: A final blend of functional coated pellets (from Step C or Step F) along with talc and/or colloidal silicon dioxide was prepared using a V-Blender and then filled into hard gelatin capsules based on the required fill weight.

Example 2: Comparison of Dissolution Profiles of Trihexyphenidyl Hydrochloride (API (Control)) and Trihexyphenidyl Hydrochloride Drug-Layered Pellets, without Functional Coat Dissolution tests were performed for trihexyphenidyl hydrochloride (API (control)) and for trihexyphenidyl hydrochloride drug-layered pellets (Pellets 1A-1D). Pellets 1A-1D are similar in composition to Pellet 1 of Example 1, except Pellets 1A-1D do not comprise a functional coat, and have 25%, 50%, 75%, and 100% drug layering weight gain, respectively. The tests were performed in an incubator orbital shaker, in 20 ml of pH 6.8 phosphate buffer at 37° C. Drug release was measured using high performance liquid chromatography (HPLC) for API (control) and tartaric acid pellets 1A-1D at 5, 10, 20, 30, and 60 minutes. FIG. 1 shows the effects of tartaric acid on solubility of trihexyphenidyl hydrochloride at pH 6.8. FIG. 1 demonstrates that tartaric acid provides a microenvironment pH for improving dissolution of trihexyphenidyl hydrochloride at pH 6.8. API (control) without any tartaric acid, released about 0.66 mg/ml of trihexyphenidyl hydrochloride at 5 minutes, whereas the drug-layered pellets with 25% drug layer weight gain released about 1.9 mg/ml of trihexyphenidyl hydrochloride at 5 minutes, and the drug-layered pellets with 50, 75, and 100% drug layer weight gain released about 1.7 mg/ml of trihexyphenidyl hydrochloride at 5 minutes. The results show that the presence of a tartaric acid-containing core increases the amount of trihexyphenidyl hydrochloride that is released at a pH of above 5.

TABLE 4

| Composition | Pellet 1A (mg) | Pellet 1B (mg) | Pellet 1C (mg) | Pellet 1D (mg) |
|---|---|---|---|---|
| Tartaric acid | 50.00 | 50.00 | 50.00 | 50.00 |
| Seal Coat | | | | |
| Hypromellose (Methocel E5 Premium LV) | 1.92 | 1.92 | 1.92 | 1.92 |
| Triethyl citrate | 0.10 | 0.10 | 0.10 | 0.10 |
| Talc | 0.60 | 0.60 | 0.60 | 0.60 |
| Total weight | 52.62 | 52.62 | 52.62 | 52.62 |
| Drug Layer | | | | |
| Trihexyphenidyl hydrochloride | 8.30 | 16.60 | 24.90 | 33.20 |
| Hypromellose (Methocel E5 Premium LV) | 5.00 | 10.00 | 15.00 | 20.00 |
| Triethyl citrate | 0.25 | 0.50 | 0.75 | 1.00 |
| Talc | 1.00 | 2.00 | 3.00 | 4.00 |
| Total drug layer weight (mg) | 14.55 | 29.10 | 43.65 | 58.33 |

Example 3: Effect of Functional Coat on Release Rate of Trihexyphenidyl Hydrochloride Two-stage dissolution tests for trihexyphenidyl hydrochloride capsules containing THP pellets of the disclosure without any functional coat, and capsules containing THP pellets of the disclosure with 13% wt gain of the functional coat, were performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. Samples were collected at regular intervals of time, and drug release was measured using HPLC. The results are shown in FIG. 2. As illustrated by FIG. 2, the functional coat helps to reduce and/or prevent the initial burst release of trihexyphenidyl hydrochloride and provides a more even release of the active ingredient.

Example 4: Effect of Trihexyphenidyl Hydrochloride and Tartaric Acid Ratio on the Release Rate of Trihexyphenidyl Hydrochloride Two-stage dissolution tests for trihexyphenidyl hydrochloride capsules containing the formulation of Pellet 1, and trihexyphenidyl hydrochloride capsules containing the formulation of Pellet 2, were performed using USP Apparatus I at 100 RPM and 37° C., in 900 ml of 0.01 N HCl for 1 hour followed by dissolution in 900 ml of pH 6.8 phosphate buffer for 24 hours, to simulate physiological conditions. Pellets 1 and 2 contained about 13% coating wt gain of functional coat. Samples were collected at regular intervals of time and drug release was measured using HPLC. FIG. 3 demonstrates that Pellet 2 formulation, with a tartaric acid to drug ratio of 40:1, exhibits a much faster dissolution rate compared to Pellet 1 formulation, with a tartaric acid to drug ratio of 10:1, indicating that the amount of acid in the core is directly proportional to the dissolution rate of the drug at pH 6.8.

Example 5: Comparison of Trihexyphenidyl Hydrochloride Release Profile from Pellet 1 Formulation and Marketed Trihexyphenidyl Hydrochloride Tablets, 5 mg, in pH 6.8 Phosphate Buffer Dissolution tests for trihexyphenidyl hydrochloride capsules containing Pellet 1 formulation and marketed IR trihexyphenidyl hydrochloride tablets, 5 mg, were performed using USP Apparatus I at 100 RPM and 37° C., in 900 ml of pH 6.8 phosphate buffer for 24 hours. Samples were collected at regular intervals of time and drug release was measured using HPLC. FIG. 4 demonstrates that the marketed IR trihexyphenidyl hydrochloride tablet exhibits faster dissolution rate of THP compared to Pellet 1 formulation. FIG. 4 demonstrates that the marketed trihexyphenidyl hydrochloride tablet provides initial burst release of THP, whereas the Pellet 1 formulation provides no initial burst release of THP. The slow release of trihexyphenidyl from the Pellet 1 formulation is attributed to the presence of controlled release membrane comprising ethyl cellulose and hypromellose phthalate (HP 55). Further, tartaric acid provides a microenvironmental pH for improving drug solubility and recovery (by the end of 24 hours) of trihexyphenidyl hydrochloride, even at pH 6.8.

Example 6: Effect of Ethyl Cellulose and Hypromellose Phthalate Ratio on Trihexyphenidyl Hydrochloride Dissolution Profile Two-stage dissolution tests for trihexyphenidyl hydrochloride capsules containing Pellet 7 [ethyl cellulose:hypromellose phthalate (80:20)] formulation, and for trihexyphenidyl hydrochloride capsules containing Pellet 8 [ethyl cellulose:hypromellose phthalate (85:15)] formulation, were performed using USP Apparatus I at 100 RPM and 37° C., in 900 ml of 0.01 N HCl for one hour followed by dissolution in 900 ml of pH 6.8 phosphate buffer for 24 hours, to simulate physiological conditions. Samples were collected at regular intervals of time and drug release was measured using HPLC. FIG. 5 compares the dissolution profiles of capsules containing Pellets 7 and 8. FIG. 5 demonstrates that pellets containing a higher amount of ethocel (Pellet 8) provide a reduced drug release rate and more controlled release compared to pellets containing a lower amount of ethocel (Pellet 7).

Example 7: Effect of Functional Coat on Release Rate of Trihexyphenidyl Hydrochloride Two-stage dissolution tests for trihexyphenidyl hydrochloride capsules containing pellets 5, 11, 12, or 13 with 25%, 20%, 30%, or 35% wt gain, respectively, of the functional coat were performed using USP Apparatus I at 100 RPM and 37° C., in 900 ml of pH 1.2 medium for 1 hour followed by dissolution in 900 ml of pH 6.8 phosphate buffer for 24 hours, to simulate physiological conditions. Samples were collected at regular intervals of time, and drug release was measured using HPLC. The results of the Experiment are illustrated in FIG. 6. FIG. 6 demonstrates that the drug release rate increases with decreasing functional coat weight gain. As shown in FIG. 6, pellets with 20% wt gain of the functional coat provided the fastest release and pellets with 35% wt gain of the functional coat provided the slowest release rate.

Example 8: Comparison of Trihexyphenidyl Hydrochloride Release Profile from Pellets with and without an Immediate Release Drug Layer Two-stage dissolution tests for trihexyphenidyl hydrochloride capsules containing Pellets 5, 15, or 16 were performed using USP Apparatus I at 100 RPM and 37° C., in 900 ml of pH 1.2 HCl for one hour followed by dissolution in 900 ml of pH 6.8 phosphate buffer for 24 hours, to simulate physiological conditions. Samples were collected at regular intervals of time, and drug release was measured using HPLC. Pellet 5 contained 5 mg of trihexyphenidyl hydrochloride in drug layer-1 (ER layer) and contained no drug layer-2 (IR layer); Pellet 15 contained 5.1 mg of trihexyphenidyl hydrochloride in drug layer-1 and 0.9 mg of trihexyphenidyl hydrochloride in drug layer-2; and Pellet 16 contained 6.37 mg of trihexyphenidyl hydrochloride in drug layer-1 and 1.125 mg of trihexyphenidyl hydrochloride in drug layer-2. FIG. 7 demonstrates that Pellet 5 (without drug layer-2) exhibits a lag time to therapeutic drug concentration of about 2 hours, and Pellets 15 and 16 (containing drug layer-2) exhibit a lag time to therapeutic drug concentration of about 30 minutes.

Example 9: Comparison of Dissolution Profile of Pellets Containing a Combination of pH Independent Water-Insoluble Polymer and an Enteric Polymer; and Pellets Containing a Combination of Two Enteric Polymers Two-stage dissolution tests for trihexyphenidyl hydrochloride capsules containing Pellet 3 [ethyl cellulose:hypromellose phthalate (85:15)] formulation, trihexyphenidyl hydrochloride capsules containing Pellet 4 [ethyl cellulose: hypromellose (85:15)] formulation, and trihexyphenidyl hydrochloride capsules containing Pellet 6 [Eudragit® S 100: Hypromellose phthalate (85:15)] formulation were performed using USP Apparatus I at 100 RPM and 37° C., in 900 ml of pH 1.2 medium for one hour followed by dissolution in 900 ml of pH 6.8 phosphate buffer for 24 hours, to simulate physiological conditions. Samples were collected at regular intervals of time and drug release was measured using HPLC. FIG. 9 compares the two-stage dissolution profiles of Pellets 3, 4, and 6. FIG. 9 demonstrates that the type of water-insoluble polymer and the type of pore former in the functional coat plays a critical role in controlling the release rate of trihexyphenidyl hydrochloride. FIG. 9 demonstrates that Pellet 3 containing ethocel and hypromellose phthalate (HP 55) provides more controlled release of the drug compared to Pellet 4 containing ethocel and hypromellose (Methocel E5 Prem LV), and Pellet 6 containing Eudragit S100 and hypromellose phthalate (HP 55) in the functional coat.

The present disclosure is well adapted to attain the ends and advantages mentioned, as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified, and all such variations, including but not limited to substitution of different opioid active agents, are considered within the scope and spirit of the present disclosure. Various publications, patents, and patent application are cited herein, the contents of which are hereby incorporated-by-reference herein in their entireties.

The invention claimed is:

1. A pharmaceutical pellet composition comprising:
   a) a core comprising an organic acid;
   b) a first drug layer encompassing at least a portion of the core, wherein the first drug layer comprises trihexyphenidyl or a pharmaceutically acceptable salt thereof; and
   c) a functional coat encompassing at least a portion of the drug layer, wherein the functional coat comprises a nonionic water-insoluble polymer and a pore former, and
   wherein the composition provides extended release of trihexyphenidyl or a pharmaceutically acceptable salt thereof, with a $C_{min}$:$C_{max}$ ratio of ≥0.4, for a period of at least 12 hours,
   wherein the trihexyphenidyl or a pharmaceutically acceptable salt thereof, and the organic acid are present in a weight ratio of from about 1:10 to about 1:100,
   wherein the trihexyphenidyl or the pharmaceutically acceptable salt thereof is present in an amount of from about 0.5% w/w to about 10% w/w, based on the total weight of the composition,
   wherein the nonionic water-insoluble polymer and the pore former are present in a weight ratio from-about 60:40 and about 99.5:0.5, and
   wherein the functional coat has a coating weight gain of from about 25% w/w to about 35% w/w, based on the total weight of the pellet without the functional coat.

2. The composition of claim 1, wherein the composition provides a therapeutic plasma concentration of from about 1 ng/ml to about 20 ng/ml.

3. The composition of claim 1, wherein the core consists of one or more organic acids.

4. The composition of claim 1, wherein the core is a nonpareil seed coated with an organic acid layer.

5. The composition of claim 1, wherein the organic acid is selected from the group consisting of tartaric acid, citric acid, fumaric acid, succinic acid, malic acid, and combinations thereof.

6. The composition of claim 1, wherein the first drug layer further comprises a nonionic water-soluble polymer that is methyl cellulose and/or hydroxypropyl methylcellulose.

7. The composition of claim 1, wherein the nonionic water-insoluble polymer is present in an amount of from about 8% to about 25% w/w, based on the total weight of the composition and is selected from the group consisting of ethyl cellulose, cellulose acetate, a polyvinyl acetate dispersion, and combinations thereof.

8. The composition of claim 1, wherein the pore former is an enteric polymer selected from the group consisting of cellulose acetate phthalate, cellulose acetate succinate, methylcellulose phthalate, hydroxyethyl cellulose phthalate, polyvinyl acetate phthalate, polyvinyl butyrate acetate, vinyl acetate-maleic anhydride copolymer, methacrylic acid copolymer, hydroxypropyl methylcellulose phthalate, polyvinyl acetate phthalate, cellulose acetyl phthalate, and combinations thereof.

9. The composition of claim 1, wherein the pore former is a nonionic, water-soluble polymer selected from the group consisting of methyl cellulose, hydroxypropyl cellulose, hydroxypropyl methylcellulose, polyethylene glycol, and mixtures thereof.

10. The composition of claim 1, wherein the pore former is a plasticizer selected from the group consisting of glycerin, polyethylene glycol monomethyl ether, triethyl citrate, triacetin, polyethylene glycol, propylene glycol, sorbitol sorbitan solution, dibutyl sebacate, and mixtures thereof.

11. The composition of claim 1, wherein the composition further comprises a second drug layer comprising trihexyphenidyl or a pharmaceutically acceptable salt thereof.

12. A therapeutic method for treating dystonia, sialorrhea, or dyskinesia, the method comprising orally administering to a subject in need thereof an extended release trihexyphenidyl composition comprising:
  a) a core comprising an organic acid;
  b) a drug layer encompassing at least a portion of the core, wherein the drug layer comprises trihexyphenidyl or a pharmaceutically acceptable salt thereof; and
  c) a functional coat encompassing at least a portion of the drug layer, wherein the functional coat comprises a nonionic water-insoluble polymer and a pore former,
  wherein the composition is for oral administration,
  wherein the composition provides extended release of trihexyphenidyl or a pharmaceutically acceptable salt thereof, with a $C_{min}:C_{max}$ ratio of $\geq 0.4$, for a period of at least about 12 hours,
  wherein the trihexyphenidyl or a pharmaceutically acceptable salt thereof, and the organic acid are present in a weight ratio of from about 1:10 to about 1:100,
  wherein the trihexyphenidyl or the pharmaceutically acceptable salt thereof is present in an amount of from about 0.5% w/w to about 10% w/w, based on the total weight of the composition,
  wherein the nonionic water-insoluble polymer and the pore former are present in a weight ratio from-about 60:40 and about 99.5:0.5, and
  wherein the functional coat has a coating weight gain of from about 25% w/w to about 35% w/w, based on the total weight of the pellet without the functional coat.

13. The method of claim 12, wherein the composition is administered once a day.

14. A method for improving patient compliance, the method comprising orally administering to a patient in need thereof, an extended release trihexyphenidyl composition comprising,
  a) a core comprising an organic acid;
  b) a drug layer encompassing at least a portion of the core, wherein the drug layer comprises trihexyphenidyl or a pharmaceutically acceptable salt thereof; and
  c) a functional coat encompassing at least a portion of the drug layer,
  wherein the functional coat comprises a nonionic water-insoluble polymer and a pore former,
  wherein the composition provides extended release of trihexyphenidyl or a pharmaceutically acceptable salt thereof, with a Cmin:Cmax ratio of $\geq 0.4$, for a period of at least 12 hours, and
  wherein the composition reduces side effects associated with high peak serum concentration (Cmax) and low trough-to-peak concentration ratios (Cmin:Cmax) of <0.4.

15. The method of claim 14, wherein the side effects include drowsiness, dizziness or blurred vision, dry mouth, stomach upset, vomiting, diarrhea, constipation, and difficulty in urinating, or combinations thereof.

16. The method of claim 14, wherein the composition is a pellet composition suitable for dosing in capsules, sachets, or as sprinkles on food.

17. A method of making a pharmaceutical pellet composition comprising trihexyphenidyl or a pharmaceutically acceptable salt thereof, the method comprising: coating a core comprising an organic acid with a drug layer comprising trihexyphenidyl or a pharmaceutically acceptable salt thereof to obtain a drug layered core, and coating the drug layered core with a functional coat comprising a nonionic water-insoluble polymer and a pore former,
  Wherein the nonionic water-insoluble polymer is selected from the group consisting of ethyl cellulose, cellulose acetate, a polyvinyl acetate dispersion, and combinations thereof,
  wherein the pore former is a nonionic water-soluble polymer, an enteric polymer, or a plasticizer;
  wherein the core consists of one or more organic acids, or is a nonpareil seed coated with an organic acid layer;
  wherein the composition provides extended release of trihexyphenidyl or a pharmaceutically acceptable salt thereof, with a $C_{min}:C_{max}$ ratio of $\geq 0.4$
  wherein the trihexyphenidyl or a pharmaceutically acceptable salt thereof, and the organic acid are present in a weight ratio of from about 1:10 to about 1:100,
  wherein the trihexyphenidyl or the pharmaceutically acceptable salt thereof is present in an amount of from about 0.5% w/w to about 10% w/w, based on the total weight of the composition,
  wherein the nonionic water-insoluble polymer and the pore former are present in a weight ratio from-about 60:40 and about 99.5:0.5, and
  wherein the functional coat has a coating weight gain of from about 25% w/w to about 35% w/w, based on the total weight of the pellet without the functional coat.

* * * * *